(12) United States Patent
Mielke et al.

(10) Patent No.: US 10,093,918 B2
(45) Date of Patent: Oct. 9, 2018

(54) SAMPLE COLLECTION AND ANALYSIS DEVICES

(71) Applicant: Lucigen Corporation, Middleton, WI (US)

(72) Inventors: Cindy Mielke, Waunakee, WI (US);
Kyle Williamson, Oregon, WI (US);
James Koelbl, Cross Plains, WI (US);
Dylann Ceriani, San Diego, CA (US);
Chris da Costa, Vista, CA (US); Espir Kahatt, Carlsbad, CA (US)

(73) Assignee: LUCIGEN CORPORATION, Middleton, WI (US)

( * ) Notice: Subject to any disclaimer, the term of this patent is extended or adjusted under 35 U.S.C. 154(b) by 381 days.

(21) Appl. No.: 14/729,760

(22) Filed: Jun. 3, 2015

(65) Prior Publication Data

US 2015/0353919 A1  Dec. 10, 2015

Related U.S. Application Data

(60) Provisional application No. 62/007,544, filed on Jun. 4, 2014.

(51) Int. Cl.
*B01L 3/00* (2006.01)
*C12N 15/10* (2006.01)
(Continued)

(52) U.S. Cl.
CPC .......... *C12N 15/1017* (2013.01); *A61B 5/157* (2013.01); *A61B 10/0045* (2013.01);
(Continued)

(58) Field of Classification Search
CPC . C12N 15/1017; A61B 10/0096; A61B 5/157; A61B 10/0045; A61B 10/02; G01N 1/38; B01L 3/502738; B01L 3/5029; B01L 7/52; B01L 7/00; B01L 2300/123; B01L 2400/0481; B01L 2200/0689;
(Continued)

(56) References Cited

U.S. PATENT DOCUMENTS 4,806,316 A  2/1989  Johnson et al.
4,857,274 A  8/1989  Simon
(Continued)

FOREIGN PATENT DOCUMENTS

BE  849898 A1  6/1977
EP  2181932 A1  5/2010
(Continued)

OTHER PUBLICATIONS

Pancholi et al., Detection of Toxigenic *Clostridium difficile*: Comparison of the Cell Culture Neutralization, Xpert C. *difficile*, XPert C. *difficile*/Epi, and Illumigene C. *difficile* Assays, J. Clin. Microbiol, Apr. 2012: 50(4): 1331-1335

*Primary Examiner* — Jill A Warden
(74) *Attorney, Agent, or Firm* — Daniel A. Blasiole; Joseph T. Leone; DeWitt Ross & Stevens S.C.

(57) ABSTRACT

Devices and methods for collecting, processing, and analyzing a sample. A sample collection module is configured for collecting, mixing diluting, and filtering a sample for analysis. A reaction cartridge is configured for processing a sample, mixing it with dried reagents, and conducting a chemical reaction for detecting target analytes.

30 Claims, 16 Drawing Sheets

(51) Int. Cl.
*A61B 10/00* (2006.01)
*A61B 10/02* (2006.01)
*A61B 5/157* (2006.01)
*C12Q 1/6806* (2018.01)
*B01L 7/00* (2006.01)
*G01N 1/38* (2006.01)

(52) U.S. Cl.
CPC .......... *A61B 10/0096* (2013.01); *A61B 10/02* (2013.01); *B01L 3/5029* (2013.01); *B01L 3/502738* (2013.01); *B01L 7/52* (2013.01); *C12Q 1/6806* (2013.01); *B01L 7/00* (2013.01); *B01L 2200/0689* (2013.01); *B01L 2200/10* (2013.01); *B01L 2300/042* (2013.01); *B01L 2300/043* (2013.01); *B01L 2300/0681* (2013.01); *B01L 2300/087* (2013.01); *B01L 2300/123* (2013.01); *B01L 2400/0481* (2013.01); *B01L 2400/0487* (2013.01); *B01L 2400/06* (2013.01); *B01L 2400/0655* (2013.01); *G01N 1/38* (2013.01)

(58) Field of Classification Search
CPC ......... B01L 2300/042; B01L 2300/043; B01L 2300/0681; B01L 2400/0655; B01L 2400/0487; B01L 2300/087; B01L 2200/10; B01L 2400/06; C12Q 1/6806
See application file for complete search history.

(56) References Cited

U.S. PATENT DOCUMENTS

| | | |
|---|---|---|
| 4,902,624 A | 2/1990 | Columbus et al. |
| 4,918,025 A | 4/1990 | Grenner |
| 4,940,527 A | 7/1990 | Kazlauskas et al. |
| 4,963,498 A | 10/1990 | Hillman et al. |
| 5,104,813 A | 4/1992 | Besemer et al. |
| 5,133,937 A | 7/1992 | Frackleton et al. |
| 5,143,084 A | 9/1992 | Macemon et al. |
| 5,147,606 A | 9/1992 | Charlton et al. |
| 5,223,219 A | 6/1993 | Subramanian et al. |
| 5,229,297 A | 7/1993 | Schnipelsky et al. |
| 5,244,630 A | 9/1993 | Khalil et al. |
| 5,374,522 A | 12/1994 | Murphy et al. |
| 5,399,486 A | 3/1995 | Cathey et al. |
| 5,498,392 A | 3/1996 | Wilding et al. |
| 5,605,662 A | 2/1997 | Heller et al. |
| 5,627,041 A | 5/1997 | Shartle |
| 5,627,071 A | 5/1997 | Triva |
| 5,746,978 A | 5/1998 | Bienhaus et al. |
| 5,798,215 A | 8/1998 | Cathey et al. |
| 5,856,174 A | 1/1999 | Lipshutz et al. |
| 5,863,502 A | 1/1999 | Southgate et al. |
| 5,882,903 A | 3/1999 | Andrevski et al. |
| 5,922,591 A | 7/1999 | Anderson et al. |
| 5,948,673 A | 9/1999 | Cottingham |
| 5,955,351 A | 9/1999 | Gerdes et al. |
| 5,958,349 A | 9/1999 | Petersen et al. |
| 5,976,824 A | 11/1999 | Gordon |
| 6,004,512 A | 12/1999 | Titcomb et al. |
| 6,043,080 A | 3/2000 | Lipshutz et al. |
| 6,168,948 B1 | 1/2001 | Anderson et al. |
| 6,197,595 B1 | 3/2001 | Anderson et al. |
| 6,410,278 B1 | 6/2002 | Notomi et al. |
| 6,440,725 B1 | 8/2002 | Pourahmadi et al. |
| 6,565,815 B1 | 5/2003 | Chang et al. |
| 6,664,104 B2 | 12/2003 | Pourahmadi et al. |
| 6,743,605 B1 | 6/2004 | Rabbani et al. |
| 6,764,821 B1 | 7/2004 | Rabbani et al. |
| 6,783,736 B1 | 8/2004 | Taylor et al. |
| 6,818,185 B1 | 11/2004 | Petersen et al. |
| 6,921,639 B2 | 7/2005 | Vischer |
| 7,208,072 B2 | 4/2007 | Amirkhanian et al. |
| 7,294,478 B1 | 11/2007 | Hinchcliffe |
| 7,309,409 B2 | 12/2007 | Amirkhanian et al. |
| 7,435,575 B2 | 10/2008 | Vischer |
| 7,468,245 B2 | 12/2008 | Rabbani et al. |
| 7,485,417 B2 | 2/2009 | Rabbani et al. |
| 7,491,527 B2 | 2/2009 | Yuan et al. |
| 7,494,790 B2 | 2/2009 | Notomi et al. |
| 7,553,647 B2 | 6/2009 | Yuan et al. |
| 7,622,083 B2 | 11/2009 | Amirkhanian et al. |
| 7,678,576 B2 | 3/2010 | Sasaki et al. |
| 7,713,691 B2 | 5/2010 | Rabbani et al. |
| 7,727,472 B2 | 6/2010 | Nagaoka et al. |
| 7,754,476 B2 | 7/2010 | Itoh et al. |
| 7,854,897 B2 | 12/2010 | Tanaami et al. |
| 7,858,045 B2 | 12/2010 | Tanaami et al. |
| 7,988,913 B2 | 8/2011 | Numajiri |
| 8,105,783 B2 | 1/2012 | Handique |
| 8,114,027 B2 | 2/2012 | Triva |
| 8,133,989 B2 | 3/2012 | Rabbani et al. |
| 8,168,442 B2 | 5/2012 | Petersen et al. |
| 8,178,056 B2 | 5/2012 | Yokoyama |
| 8,206,902 B2 | 6/2012 | Mitani et al. |
| 8,226,906 B2 | 7/2012 | Saul |
| 8,288,092 B2 | 10/2012 | Rabbani et al. |
| 8,317,728 B2 | 11/2012 | Triva |
| 8,354,080 B2 | 1/2013 | Tsao et al. |
| 8,415,103 B2 | 4/2013 | Handique |
| 8,425,864 B2 | 4/2013 | Haywood et al. |
| 8,445,664 B2 | 5/2013 | Rabbani et al. |
| 8,460,620 B2 | 6/2013 | Bartfeld et al. |
| 8,470,153 B2 | 6/2013 | Feiglin et al. |
| 8,486,633 B2 | 7/2013 | Rabbani et al. |
| 8,551,761 B2 | 10/2013 | Gohring et al. |
| 8,623,789 B2 | 1/2014 | Belgrader et al. |
| 8,632,740 B2 | 1/2014 | Dastane et al. |
| 8,906,621 B2 | 12/2014 | You |
| 2005/0208539 A1* | 9/2005 | Vann ................ B01L 3/502707 435/6.11 |
| 2006/0076068 A1 | 4/2006 | Young et al. |
| 2007/0166199 A1 | 7/2007 | Zhou et al. |
| 2008/0223485 A1 | 9/2008 | Nyambi |
| 2012/0083018 A1 | 4/2012 | Schoenfeld et al. |
| 2013/0130262 A1 | 5/2013 | Battrell et al. |

FOREIGN PATENT DOCUMENTS

| | | |
|---|---|---|
| FR | 2296172 A1 | 7/1976 |
| WO | WO 2012/047030 A2 | 4/2012 |
| WO | WO PCT/US2015/ 034015 | 10/2015 |

* cited by examiner

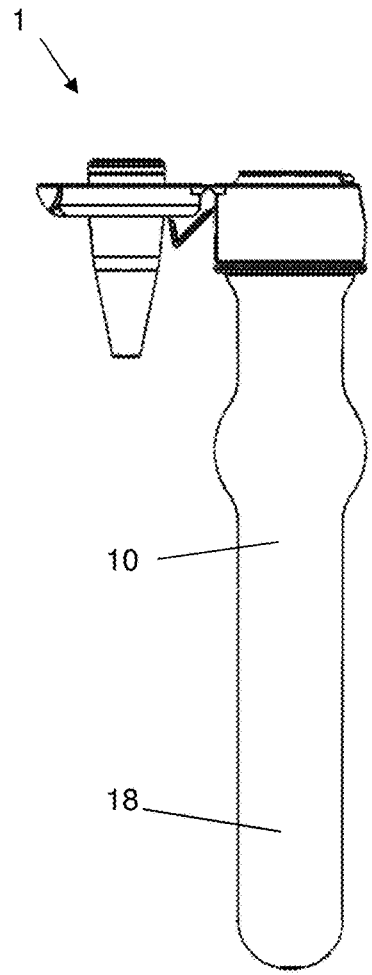
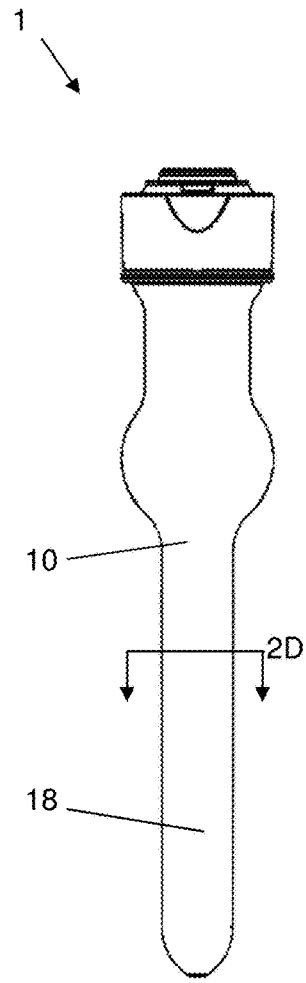
FIG. 2B
FIG. 2C
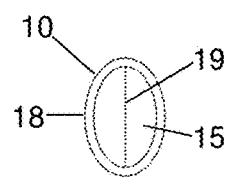
FIG. 2D

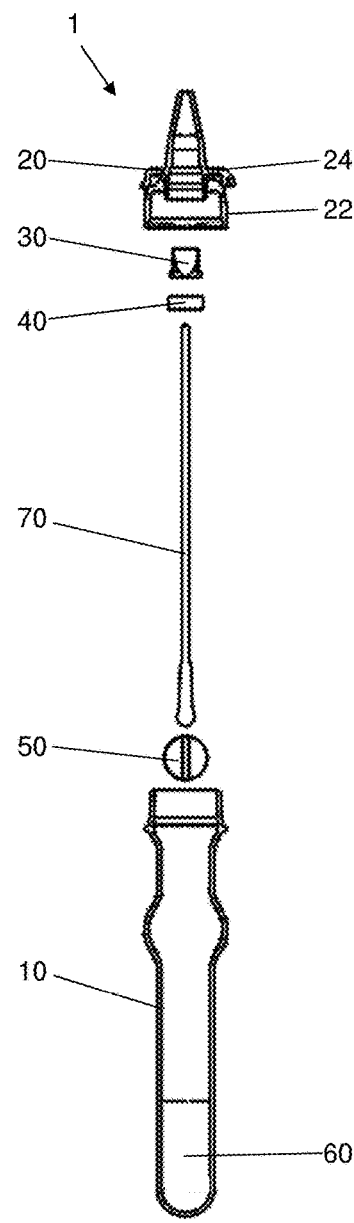
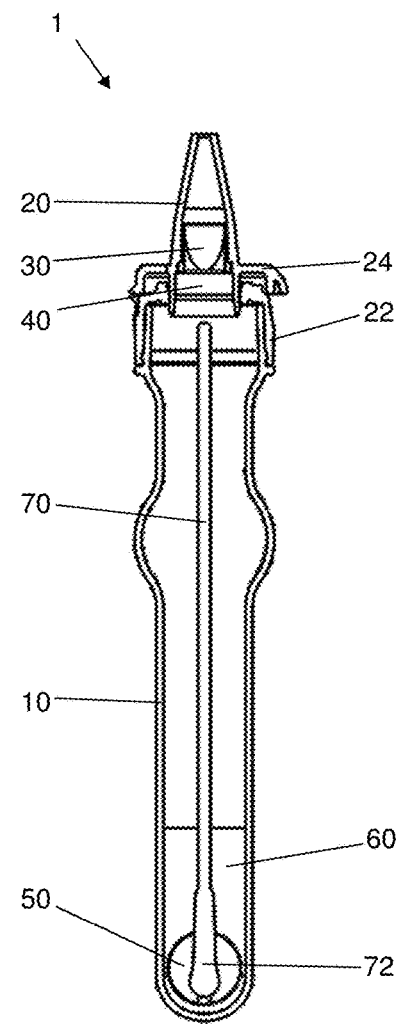
FIG. 4A
FIG. 4B

SAMPLE COLLECTION AND ANALYSIS DEVICES

FIELD OF THE INVENTION

The invention is directed to a system for collecting, processing, and analyzing samples.

BACKGROUND

Accurate and rapid diagnostic tests help improve patient outcome and help contain the spread of disease. Recent adaptation of molecular methodologies has led to more accurate and sensitive molecular diagnostic tests. PCR, RT-PCR, DNA array and DNA sequencing have proven to be highly sensitive and specific. More recently, loop mediated isothermal amplification (LAMP) has proven to be an attractive technology for rapid detection of pathogens. Due to high sensitivity and rapid turnaround time, molecular diagnostic tests are increasingly being used in large clinical laboratories.

Molecular analysis of clinical samples for the detection of genetic materials typically involves nucleic acid amplification, which typically entails a series of steps starting at sample collection. Raw samples are rarely suitable for direct detection of nucleic acids, necessitating processing of the sample prior to nucleic acid amplification. Significant resources and time are spent for clinical sample processing that involves multiple mechanical, physical, and chemical treatments before a target nucleic acid can be amplified for detection. One common approach in sample processing has been suspending a small aliquot of the sample in sample buffer followed by filtration to remove particulate material. Such a method is utilized in the Illumigene *Clostridium difficile* Test manufactured by Meridian Biosciences (*J. Clin. Microbiol*. April 2012; 50(4): 1331-1335). However, such methods involve multiple steps, require operators to transfer a measured quantity from one step to the next, and are time consuming, making them unsuitable to be used at the point of care, such as emergency room, nursing homes, and physician's office. Another common approach to isolate nucleic acids from clinical samples has been cell lysis followed by binding to resins followed by washing and finally elution with buffer for subsequent application. Such a process is either carried out by a highly trained technician or requires expensive equipment for automation. Neither option is suitable in a point-of-care setting.

There has been a growing trend and desire to move clinical diagnostic tests out of large central laboratories to point-of-care settings for faster and optimal treatment decisions. Having a diagnostic test that can be run at the point of care is expected to lead to better outcomes for the patient and cost savings. For the sample processing system to be useful at the point-of-care setting, it must involve very few steps and preferably comprises a single device that combines multiple steps. Such a device also should be able to accommodate a wide variety of clinical samples such as blood, saliva, stool etc. A point-of-care device should not require measuring equipment for volume etc., as access to such equipment may not exist or operators may not have training to use such equipment.

The challenge in developing a point-of-care diagnostic test has been developing a test that is easy to conduct, is small enough to fit in a point-of-care setting, is low cost to adopt and run, can accommodate diverse clinical samples, and yet can retain the high sensitivity and rapid turnaround time of larger instruments used in central laboratories. The lack of a point-of-care molecular diagnostic test underlines the need for the methods and devices described herein.

SUMMARY OF THE INVENTION

The present invention is directed to a system for collecting, processing, and analyzing samples, such as biological samples, environmental samples, etc. The system includes a sample collection module and a reaction cartridge. The sample collection module is configured for collecting, diluting, and filtering a sample. The reaction cartridge is configured for processing the sample, adding reaction reagents to the sample, and conducting one or more chemical reactions with the sample. In some versions, the reaction cartridge is configured for mixing reagents, heat extracting nucleic acids, conducting a plurality of parallel chemical reactions, and optically detecting a plurality of reaction products using a single disposable cartridge.

An exemplary version of the sample collection module includes a capped, flexible tube containing sample buffer. The cap is a rigid cap fitted internally with a filter. The filter is initially protected from the sample buffer by a liquid-impermeable seal in the cap. The cap is preferably configured to be opened while keeping at least part of it attached to the tube. Opening the cap provides access to the inside of the tube to introduce a sample in the sample buffer. The sample may be introduced using a swab, a pick, or some other sampling device. After introducing the sample to the sample buffer, the tube can be inverted and squeezed to filter and dispense the sample-containing sample buffer. The process of inverting the sample collection module acts as a step for mixing the sample with the sample buffer.

The seal that initially separates the filter from the sample buffer may take the form of a removable liquid-impermeable membrane or a plug disposed within the cap. If a plug is included, the cap is configured such that opening the cap dislodges the plug from the cap and allows the sample buffer to contact the filter when the sample collection module is inverted.

The filter may comprise a plurality of filter layers. The filter is preferably configured to remove large particulate matter from the sample. For example, the filter may be composed of porous synthetic materials that allow fluid and analyte such as bacteria and virus particles to pass through while acting as a barrier to large particulate materials. The filter may also or alternatively be configured to bind to assay interferents of downstream assays. Non-limiting examples of interferents, such as interferents in a nucleic acid amplification assay as described herein, include bile salts (e.g., from feces), complex polysaccharide (e.g., from feces), heme (e.g. from blood), hemoglobin (e.g., from blood), proteinases (e.g., from milk), and humic acid (e.g., from soil). A polypropylene filter may be used to preferentially remove the interferents, such as the polysaccharides. A matrix, such as a gel filtration resin, may be sandwiched between two filters layers for removing salts.

The sample buffer may contain reagents that stabilize the analyte or sample (e.g., ethylenediaminetetraacetic acid (EDTA) and buffering agent such as Tris buffer), extract nucleic acids from the sample (e.g., reducing agents such as TCEP (tris(2-carboxyethyl)phosphine)), inhibit microbial growth or at least not promote microbial growth (e.g., antifungal agents such as amphotericin), and help with downstream chemical reactions, such as nucleic acid amplification reactions (e.g., bovine serum albumin, other types of albumin). The sample buffer may also serve as a sample dilution buffer and assay buffer. The sample dilution factor may be metered by adjusting the volume of sample buffer from 1 ml to 5 ml, for example. The sample buffer may contain exogenously added nucleic acid fragments, viral particles, or bacterial cells to be used as a process control in downstream reactions.

The sampling device (e.g., the swab, pick, etc.), may have circular ridges at the sampling end. The volume of sample can be metered by the number and diameter of circular ridges at the sampling end.

In a single disposable body, the sample collection module combines functionalities for sample collection, sample buffering, sample dilution, assay buffer addition, sample stabilization, sample processing, sample mixing, and sample filtration.

An exemplary method of using the exemplary sample collection module comprises collecting a sample with a swab or pick; opening the cap to dislodge the plug (if present) from the cap, expose the filter to the sample buffer, and provide access to the sample buffer; delivering the collected sample to the sample buffer by immersing the swab or pick in the sample buffer; closing the cap; inverting the sample collection module; and squeezing the fluid through the filter and cap nozzle to filter the sample and dispense the filtered sample into an analysis device, such as the reaction cartridge described herein.

An exemplary reaction cartridge comprises a rigid polymer frame with multiple chambers connected by fluid channels and valves. The chambers in the reaction cartridge include a sample collection chamber, a sample mixing chamber, a master mix chamber, and one or more reaction chambers. The sample collection chamber is configured for accepting liquid sample (such as from the sample collection module of the invention). The sample mixing chamber is configured for processing the sample, such as lysing any cells in the sample and/or extracting nucleic acids. The processing in the sample mixing chamber may comprise one or more of chemical treatment, heat treatment, enzymatic treatment, and physical separation from contaminants. The master mix chamber is configured for adding reagents required for nucleic acid amplification to the sample. The master mix chamber and the sample mixing chamber are coordinately configured for transferring the sample back and forth to mix the reagents added to the sample in the master mix chamber. The reaction chambers are configured for amplifying DNA or conducting other chemical reactions with the sample and detecting the reaction products, such as by optical detection.

The chambers may contain reagents suited for each of the respective processes described above. The reagents are preferably dried. The dried reagents may be air dried in situ or may be added to the chambers as lyophilized reagents. The components are mixed with the sample as the sample enters each respective chamber.

The sample is preferably moved from chamber to chamber through the fluid channels in the reaction cartridge using pressure differential. The pressure differential is preferably created by pressure actuators, such as external air or liquid pumps, which may be connected to nozzles on the cartridge. The pressure differential can be relieved through pressure vents, such as air vents, in fluidic connection with the chambers. The volume of fluid transferred may be controlled by moving the sample for a predetermined period of time or by measuring pressure build up when the destination chamber has been filled.

The valves direct the sample to the various fluid channels and chambers. Pressurized fluid may be used to actuate the valves. The pressurized fluid may comprise liquid or air. The pressurized fluid may be generated by pressure actuators, such as air or liquid pumps.

The reaction cartridge is preferably configured such that a single reaction mixture is moved to a plurality of reaction chambers. Each of the plurality of reaction chambers may have a different set of additional dried reaction components or reagents to conduct a variety of different detection assays in parallel on the same sample. The reaction mixture is preferably distributed to each of the reaction chambers via a common distribution valve. The reaction chambers may be heated for optimal reaction through contact with a heating element and/or may be cooled by air flow. The reaction chambers preferably include at least two separate optical windows, one window for illuminating reaction content and another window for detecting reaction product.

The reaction cartridge may be used with a corresponding cartridge reader capable of receiving the cartridge for the purpose of carrying out fluid movement within the cartridge, providing heat for optimal chemical reaction, illuminating reaction content, and detecting reaction products within the cartridge. The reaction cartridge and reader together preferably comprise the necessary fluidics and control systems for moving sample, mixing sample, heating sample, illuminating sample, and measuring fluorescence output from samples.

An exemplary method of using the exemplary cartridge reader includes introducing a sample into the sample collection chamber, moving a portion of the sample to the sample mixing chamber, heating the sample in the sample mixing chamber, moving the sample from the sample mixing chamber to the master mix chamber, mixing the sample with dried reagents in the master mix chamber to generate a reaction mixture, moving the reaction mixture to a plurality of reaction chambers, and conducting a plurality of reactions in the plurality of reaction wells.

The analyzed sample in the methods of the invention may be a clinical sample, an environmental sample, and/or a food sample, among others. The analyte detected preferably comprises a nucleic acid. The nucleic acid is preferably selected from the group consisting of DNA and RNA. The reactions for detecting the analyte preferably comprise nucleic acid amplification. A preferred method of nucleic acid amplification is isothermal nucleic acid amplification, such as loop-mediated isothermal amplification (LAMP) among others. The amplification product is preferably detected optically. The optical detection of the amplification product is preferably carried out in real time through the use of a fluorescent DNA detection reagent, such as SYBR green. The correctness of a formed product may be determined through DNA annealing curve analysis.

The invention also provides a sample collection and analysis system comprising a sample collection module and a reaction cartridge; a kit that comprises a sampling device (e.g., a swab, stick, pick, or applicator), a sample collection module, and a reaction cartridge; and a method of collecting and analyzing a sample comprising a method of using a sample collection module as described herein in combination with a method of using the reaction cartridge as described herein.

The objects and advantages of the invention will appear more fully from the following detailed description of the preferred embodiment of the invention made in conjunction with the accompanying drawings.

BRIEF DESCRIPTION OF THE DRAWINGS

FIG. 1A is a front exploded perspective view. FIG. 1B is a front elevation cross-sectional view. FIG. 1C is a front elevation cross-sectional view, showing the cap and its connection to the body in detail.

FIGS. 2A-2D show a sample collection module of the invention with a cap in an open position. FIG. 2A is a front elevation cross-sectional view. FIG. 2B is a front elevation view. FIG. 2C is a side elevation view. FIG. 2D is a top cross-sectional view of the device shown in FIG. 2C taken along line 2D.

FIG. 3A is a front exploded elevation view. FIG. 3B is a front elevation cross-sectional view.

FIGS. 4A and 4B show a sample collection module of the invention with the cap in a closed position after swab insertion. FIG. 4A is a front exploded cross-sectional view. FIG. 4B is a front cross-sectional view.

FIG. 8A is an exploded top/side perspective view. FIG. 8B is an exploded bottom/side perspective view.

DETAILED DESCRIPTION OF THE INVENTION

General

Figure 1A:
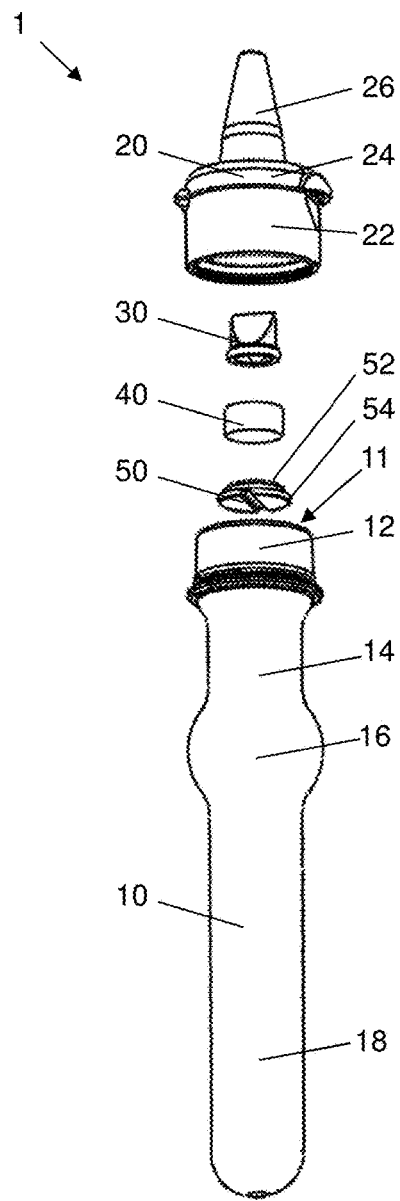
FIGS. 1A-1C show a sample collection module of the invention with the cap in a closed position in preparation for initial use.

The present invention provides devices and methods for collecting, processing, and analyzing a sample. The invention provides a sample collection module for collecting, mixing, diluting, and filtering a sample for analysis. The invention also provides a reaction cartridge for processing a sample, mixing it with dried reagents, and conducting a chemical reaction for detecting target analytes.

The sample collected and analyzed with the system and methods described herein may include any sample comprising a detectable analyte. Exemplary samples include clinical samples, environmental samples, and food samples, among others. Clinical samples include bodily fluid (e.g., blood, urine, saliva, sputum, seminal fluid, spinal fluid, mucus, or other bodily fluids), fecal matter, tissue sections, and extractions thereof, among others. Exemplary environmental samples include waste water, soil extracts, airborne spores, and a swab of an environmental surface, among others. Exemplary food samples include foods, food ingredients, and food products, among others. Other samples include plant materials or other biological samples. The samples may contain isolated or non-isolated molecules, including nucleic acids, proteins, etc.; virus particles; and/or cells, including bacterial cells, fungal cells, animal cells, and/or plant cells, etc. The sample may be in liquid form or solid form.

The analyte detected with the system and methods described herein may include any detectable analyte. The analyte may comprise any detectable molecule or biomolecule. Exemplary biomolecules include proteins and nucleic acids. Exemplary nucleic acids include single or double stranded RNA or DNA.

A preferred analyte is nucleic acid. A preferred method of detecting the nucleic acid is by amplifying the nucleic acid in the presence of a DNA detection reagent. Any method of amplifying nucleic acid is encompassed by the present invention. If the analyte is RNA, the amplification is preceded by reverse transcription.

Exemplary methods of amplifying nucleic acid include thermocycling amplification, such as the polymerase chain reaction (PCR), and isothermal amplification. A number of isothermal amplification methods are known in the art. These include transcription mediated amplification (TMA), nucleic acid sequence-based amplification (NASBA), signal mediated amplification of RNA technology (SMART), strand displacement amplification (SDA), nicking enzyme amplification reaction (NEAR), rolling circle amplification (RCA), loop-mediated isothermal amplification of DNA (LAMP), isothermal multiple displacement amplification (MDA), helicase-dependent amplification (HDA), single primer isothermal amplification (SPIA), and cross primed amplification (CPA). Any of these isothermal amplification methods are suitable for use in the present invention. Software and other methods for designing primers suitable for use in such isothermal amplification methods are well-known in the art. See, e.g., PrimerExplorer LAMP primer designing software from Eiken Chemical, Kimura et al. 2011, and others.

Preferred isothermal amplification methods are those that employ primers having a 5' end that do not bind to template DNA when the 3' is bound, having a portion complementary to downstream synthesized DNA, have a portion identical to downstream template DNA, and/or form loops by annealing to downstream synthesized DNA. Such primers are characteristic of such methods as LAMP and CPA, among others. See, e.g., Notomi et al. 2000; Xu and Hu et al. 2012; U.S. Pat. No. 6,410,278; U.S. Pat. No. 6,743,605; U.S. Pat. No. 6,764,821; U.S. Pat. No. 7,494,790; U.S. Pat. No. 7,468,245; U.S. Pat. No. 7,485,417; U.S. Pat. No. 7,713,691; U.S. Pat. No. 8,133,989; U.S. Pat. No. 8,206,902. U.S. Pat. No. 8,288,092; U.S. Pat. No. 8,445,664; U.S. Pat. No. 8,486,633; and U.S. Pat. No. 8,906,621.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

Sample Collection Module

Figure 1B:
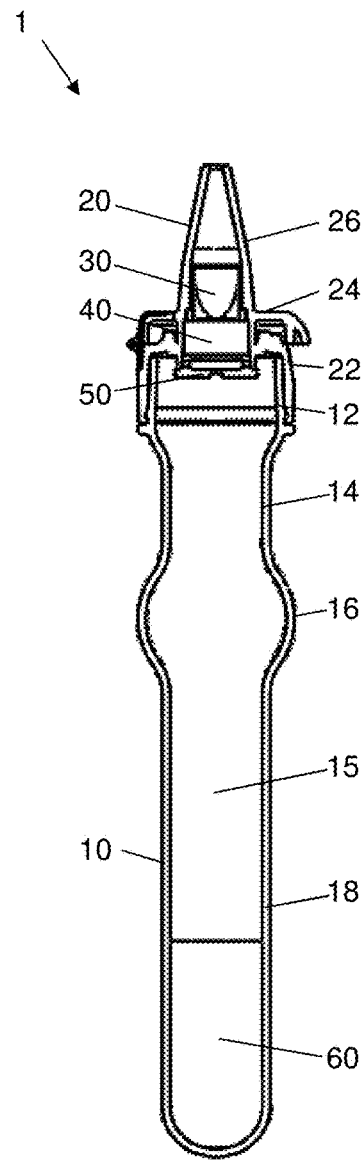
Figure 1C:
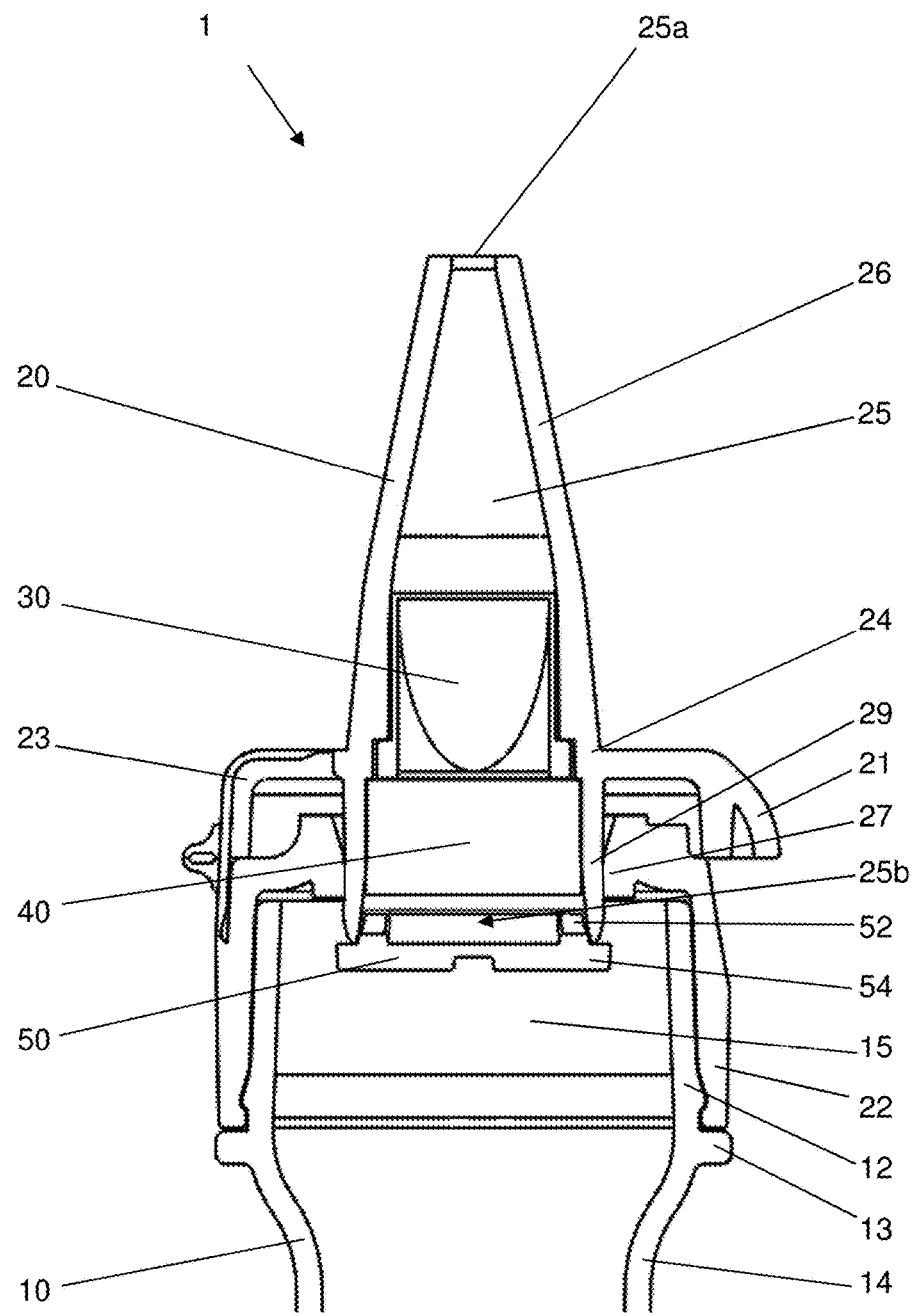

FIGS. 1A-1C show various views of an exemplary sample collection module 1 of the invention in preparation for initial use. As shown in FIGS. 1A and 1B, the exemplary sample collection module 1 generally comprises a body 10, a cap 20, a valve 30, a filter 40, and a plug 50. Of these components, at least the valve 30 and the plug 50 are optional and need not be included in the sample collection module 1 of the invention.

The body 10 is a clear, hollow, flexible (squeezable) plastic tube. The body 10 is configured to hold a liquid such as sample buffer 60, preferably at least about 5 ml of the sample buffer 60. The body 10 comprises a cap-attachment portion 12, an upper portion 14, a distended portion 16, and a lower portion 18. The cap-attachment portion 12 defines an opening 11 that leads to a body cavity 15 within the body 10 and is configured to permit attachment of the cap 20 to the body 10 in a liquid-impermeable manner. The cap 10 may reversibly attach to the cap-attachment portion 12 by snap-fit, screw-fit, or other types of fit. The distended portion 16 of the body 10 allows for finger pressure to be applied on the body 10 while squeezing the body 10. The lower portion 18 is configured define a portion of the body cavity 15 that stores the sample buffer 60 when the sample collection module 1 is in an upright position.

The cap 20 comprises a hollow cap ring 22 and a hollow cap head 24 hingedly attached to the cap ring 22. The cap ring 22 is configured to mate with the cap attachment portion 12 of the body 10 to attach the cap 20 to the body 10. As described above, the mating may be by a snap fit (as shown), a screw fit, or other types of fit. The cap head 24 is configured to form a liquid-tight seal with the cap ring 22 when the cap 20 is in a closed position as shown in FIGS. 1A and 1B. The cap head 24 also defines a hollow nozzle 26.

The valve 30 is preferably a non-return valve, such as a "duck bill valve," that permits fluid to flow only in a direction from the body 10 through the cap 20.

The filter 40 is preferably configured to permit fluid and analyte to pass through it while retaining larger particulate material. The filter 40 comprises pores preferably having a size from about 0.1 µm to about 1000 µm, more preferably from about 1 µm to about 500 µm, and more preferably from about 10 µm to about 100 µm. The average pore size is preferably from about 0.1 µm to about 1000 µm, more preferably from about 1 µm to about 500 µm, and more preferably from about 10 µm to about 100 µm. The filter 40 in some versions is devoid or substantially devoid of pores smaller than about 0.1 µm, devoid or substantially devoid of pores smaller than about 1 µm, or devoid or substantially devoid of pores smaller than about 10 µm. The filter 40 in some versions is devoid or substantially devoid of pores larger than about 1000 µm, devoid or substantially devoid of pores larger than about 500 µm, or devoid or substantially devoid of pores larger than about 100 µm. The filter 40 may comprise a polymeric material and/or other type of material. The filter 40 may comprise polyethylene, polypropylene, polyester, cellulose, cellulose derivatives (e.g., nitrocellulose), ceramic, carbon, polyphosphate, felt, and/or silicon carbide, among other materials. The filter 40 may be embedded with reagents, such as affinity reagents (e.g., antibodies, biotin, avidin, etc.) or other reagents. The filter 40 may by comprise a single filter layer or a stack of multiple filter layers. The filter 40 may comprise charged resins, porous resins, or combinations thereof. The charged resins may be sandwiched between non-charged filter layers.

The plug 50 serves as a removable liquid-impermeable seal configured to isolate the filter 40 from the sample buffer 60 prior to use, such as during storage and transport of the sample collection module 1. The plug 50 comprises a small-diameter portion 52 and a large-diameter portion 54.

A close-up of the cap 20-end of the sample collection module 1 is shown in a cross-sectional view in FIG. 1C. The cap ring 22 on the cap 20 fits on the cap-attachment portion 12 of the body 10 in a liquid-tight, snap-fit or screw-fit manner, wherein protrusions on the cap ring 22 mate with grooves on the cap-attachment portion 12 and/or protrusions on the cap-attachment portion 12 mate with grooves on the cap ring 22. A lip 13 on the body 10 between the cap-attachment portion 12 and the upper portion 14 contacts the cap ring 22 to help make a liquid-tight seal. A gasket may be included between the cap ring 22 and the cap-attachment portion 12 of the body 10 at one or more contact surfaces to facilitate a liquid-tight seal.

The cap head 24 is attached to the cap ring 22 via a hinge 23. The cap head 24 includes a handle 21 opposite the hinge 23 for gripping the cap head 24 to pivot the cap head 24 with respect to the cap ring 22 about the hinge 23. When the cap 20 is in the closed position, as shown in FIG. 1C, a tubular extension 29 of the nozzle 26 nests within an inner ring 27 defined by the cap ring 22 to create a liquid-tight seal between the body cavity 15 of the body 10 and the outside of the cap 20. A gasket may be included between the cap head 24 and the cap ring 22 at one or more contact surfaces to facilitate a liquid-tight seal. In some versions, the hinge 23 is not included and the cap head 24 is freely and completely removable from the cap ring 22.

The valve 30, the filter 40, and the small-diameter portion 52 of the plug 50 fit in a nested configuration within a nozzle cavity 25. The valve 30 is oriented within the nozzle cavity 25 of the nozzle 26 in a manner that permits fluid to flow only in a direction from second nozzle opening 25b to a first nozzle opening 25a. The small-diameter portion 52 of the plug 50 nests within the tubular extension 29 of the nozzle 26 at the second nozzle opening 25b to create a liquid-tight seal between the body cavity 15 of the body 10 and the nozzle cavity 25. The large-diameter portion 54 of the plug 50 has a diameter larger than a diameter defined by the tubular extension 29 of the nozzle 26. The large-diameter portion 54 of the plug 50 thereby extends beyond the tubular extension 29 radially with respect to the long axis of the sample collection module 1 and contacts an underside of the tubular extension 29. The large-diameter portion 54 of the plug 50 also has a diameter larger than an inner diameter defined by the inner ring 27 of the cap ring 22. In some versions, a portion of the plug 50, such as the large-diameter portion 54 fits around the tubular extension 29 of the nozzle 26 to create a liquid-tight seal between the body cavity 15 of the body 10 and the nozzle cavity 25. Such versions may serve in addition to or alternatively to the small-diameter portion 52 of the plug 50 nesting within the tubular extension 29 of the nozzle 26. Attachment of the plug 50 to the tubular extension 29 may be facilitated by protrusions in the plug 50 that nest within notches in the tubular extension 29 and/or protrusions in the tubular extension 29 that nest within notches in the plug 50.

To prepare the sample collection module 1 for use in the manner shown in FIGS. 1A-1C, the valve 30, the filter 40, and/or the plug 50 are placed into the valve cavity 25. The body cavity 15 is filled with sample buffer 60, and the cap 20 is attached to the body 10 via the cap ring 22.

Figure 2A:
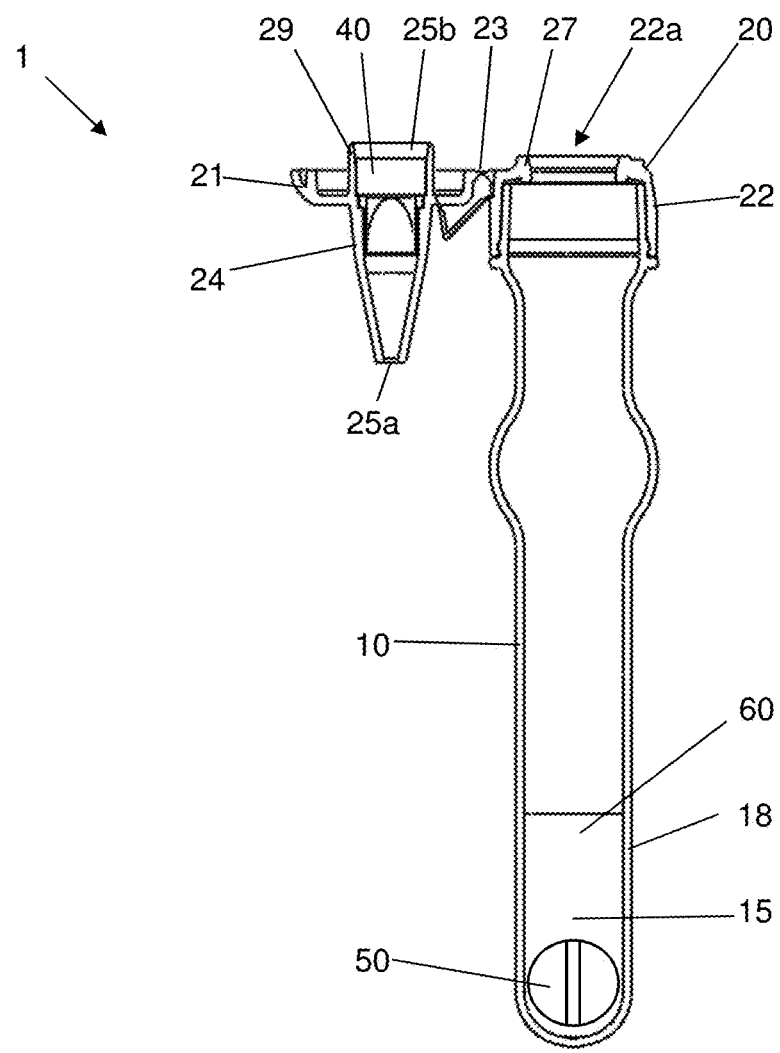

FIGS. 2A-2C show various views of a sample collection module 1 with the cap 20 in in an open position. The cap 20 is converted from the closed position, as shown in FIGS. 1A-1C, to the open position, as shown in FIGS. 2A-2C, when a user is ready to insert a sampling device in the body cavity 15 and immerse the sampling device in the sample buffer 60. The cap 20 can be converted to the open position by gripping the handle 21 on the cap head 24 and pivoting the cap head 24 with respect to the cap ring 22 about the hinge 23. Pivoting the cap head 24 with respect to the cap ring 22 slides the tubular extension 29 of the nozzle 26 through and past the inner ring 27 of the cap ring 22. As the tubular extension 29 slides past the inner ring 27, the large-diameter portion 54 of the plug 50, which has a larger diameter than an inner diameter defined by the inner ring 27, contacts the inner ring 27 and dislodges the plug 50 from the tubular extension 29 of the nozzle 26, thereby exposing the filter 40. The plug 50 falls within the body cavity 15 at the lower portion 18 of the body 10, as shown in FIG. 2A. Opening the cap 20 exposes a cap-ring opening 22a, also shown in FIG. 2A, providing access to the body cavity 15 of the body 10 and the sample buffer 60 contained therein. (In some embodiments, the sample collection module 1 is initially provided without sample buffer 60. The sample buffer 60 can be added after opening the cap 20.)

As shown in FIGS. 2B-D, particularly 2D, the lower portion 18 of the body 10 has an elliptically shaped horizontal cross section. The elliptically shaped cross section reduces the volume of sample buffer 60 required to completely cover the swab head 72 (see FIGS. 3B and 4B), while still being wide enough to allow the plug 50 to fall to the bottom of the body cavity 15 after becoming dislodged from the tubular extension 29 of the nozzle 26 (see FIG. 2A). In this manner, the greater horizontal axis 19 (dotted line) of the body cavity 15 at the lower portion 18 of the body 10 has a larger dimension than the diameter of the large-diameter portion 54 of the plug 50, and the lesser horizontal axis (horizontal axis orthogonal to the dotted line) of the body cavity 15 has a smaller dimension than the diameter of the large-diameter portion 54 of the plug 50.

Figures 3A, 3B:
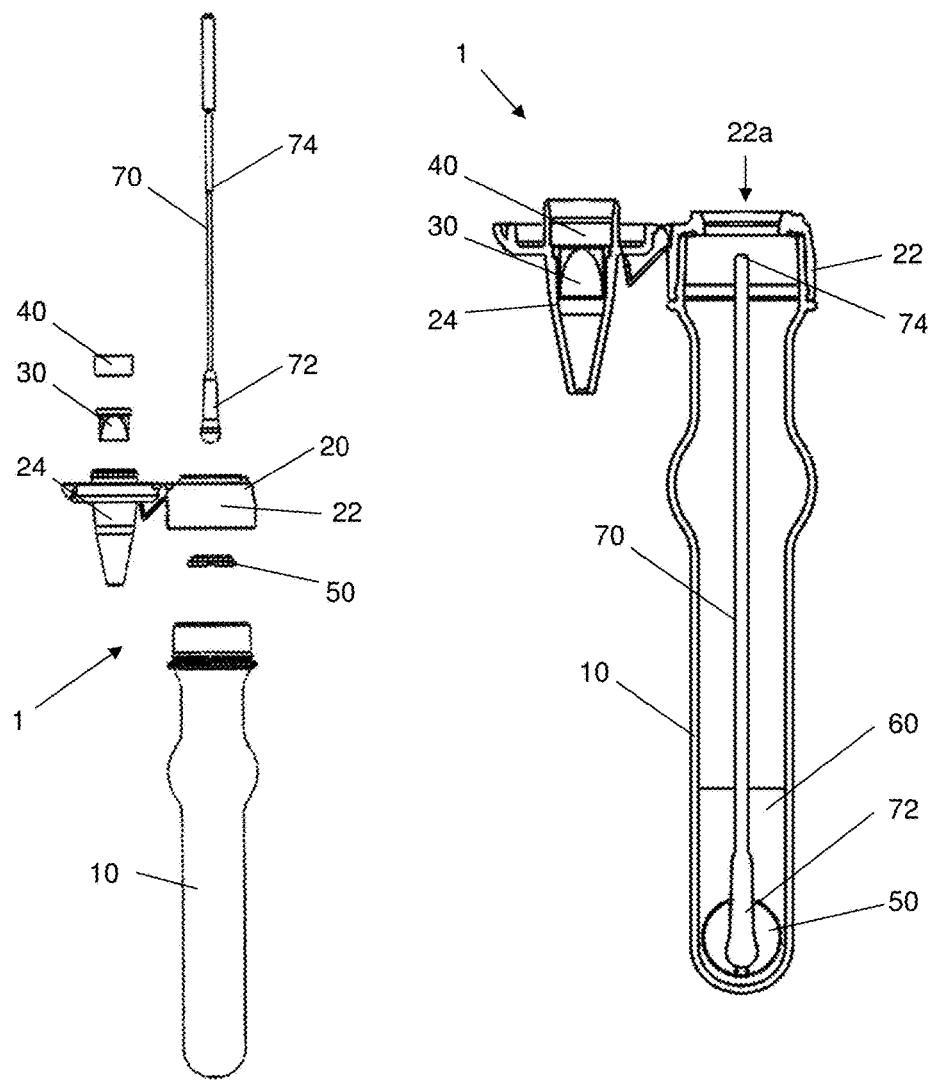
FIGS. 3A and 3B show a sample collection module of the invention with the cap in an open position during insertion of a swab.

Once the cap 20 is in an open position and the cap-ring opening 22a is exposed, a sample-containing swab 70, pick, applicator, or other sampling device is inserted through the cap-ring opening 22a and immersed in the sample buffer 60, as shown in FIGS. 3A and 3B. If a swab 70 is used, the swab head 72 is preferably fully immersed in the sample buffer 60. The swab 70 is then broken at a scored line 74. Breaking off the swab head 72 or pick into the sample collection module 1 helps reduce biohazard burden and ease of use for the operator.

As shown in FIGS. 4A and 4B, the cap 20 is returned to the closed position after the sample is immersed in the sample buffer 60 and the swab head 72 or pick is broken off. The sample collection module 1 is configured to accommodate the entire remaining length of the swab 70 after the swab head 72 is broken off. In the version shown in FIG. 4B, swab head 72 is fully immersed in the sample buffer 60 while the remaining portion of the broken-off swab 70 is only partially immersed in the sample buffer 60. The plug 50 remains resting at the bottom of the body cavity 15.

The sample buffer, now containing a biological sample, can be introduced to the reaction cartridge 100. The sample collection module 1 is inverted, and the sample buffer 60 is squeezed through the nozzle 26, sequentially passing through the second nozzle opening 25b, the filter 40, the valve 30, and the first nozzle opening 25a. The sample introduced to the reaction cartridge 100 is filtered from impurities and large particulate matter by virtue of passing the sample buffer 60 through the filter 40.

Figure 5A:
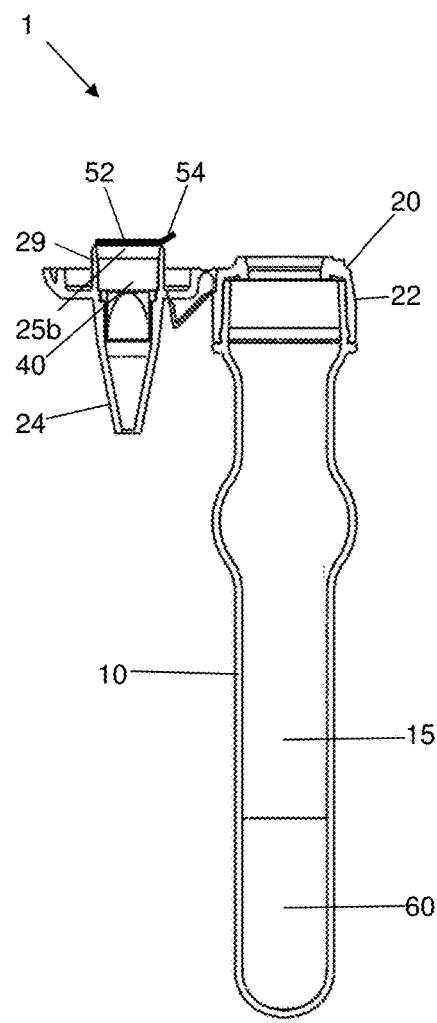
FIGS. 5A and 5B show front elevation cross-sectional views of sample collection modules of the invention comprising liquid-impermeable membranes.
Figure 5B:
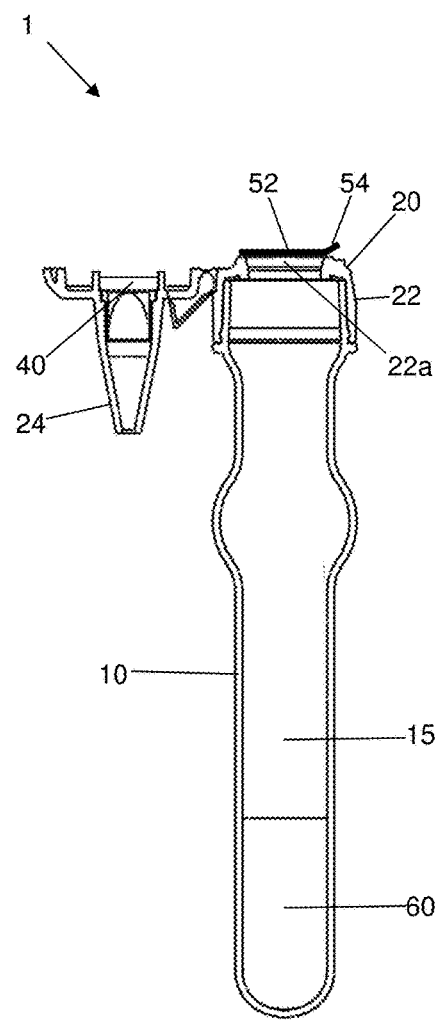

In some versions of the sample collection module 1, a liquid-impermeable seal other than the plug 50, such as a liquid-impermeable membrane 52, isolates the filter 40 from the sample buffer 60 prior to use. The liquid-impermeable membrane 52 may be disposed across the second nozzle opening 25b, as shown in FIG. 5A, or across the cap-ring opening 22a, as shown in FIG. 5B, to prevent sample buffer 60 from accessing the filter 40 when the cap 20 is in the closed position prior to use. The liquid-impermeable membrane 52 may have a tab 54 to facilitate removal of the liquid-impermeable membrane 52, such as prior to inserting a sampling device through the cap-ring opening 22a and into the sample buffer 60 or prior to filtering the sample buffer 60 after introducing a sample therein. In versions in which a liquid-impermeable membrane 52 is placed across the cap-ring opening 22a (FIG. 5B), a liquid-tight seal between the body cavity 15 and the outside of the cap 20 when the cap 20 is in the closed position is provided by a configuration other than the tubular extension 29 of the nozzle 26 nesting within the inner ring 27 of the cap ring 22, and is instead preferably provided by a portion of the cap ring 22 nesting within the cap head 24. The liquid-impermeable membrane 52 may comprise metal foil, plastic film, and/or paraffin film, among other types of liquid-impermeable films or membranes. The liquid-impermeable membrane 52 may attach to the sample collection module 1 across the second nozzle opening 25b or the cap-ring opening 22a by thermal, chemical, or physical adhesion such as through glues, resins, or other attachment media.

The sample buffer 60 may comprise a number of components to facilitate sample processing and/or preservation or to serve as controls for sample processing or downstream nucleic acid amplification and detection.

The sample buffer 60 preferably comprises a buffering agent. Any buffering agent suitable for buffering an aqueous solution at approximately neutral pH is acceptable. Suitable buffering agents are well known in the art. Examples include MES, ADA, PIPES, ACES, MOPSO, cholamine chloride, MOPS, BES, TES, HEPES, DIPSO, acetamidoglycine, TAPSO, POPSO, HEPPSO, HEPPS, tricine, glycinamide, bicine, TAPS, tris(tris(hydroxymethyl)aminomethane), TAE, and TBE, among others. The solution is preferably buffered at a pH of from about 6 to about 9.

The sample buffer 60 may also comprise a metal chelator. Exemplary metal chelators include aminopolycarboxylates (APCAs) and polyphosphonates. Exemplary APCAs include nitrilotriacetic acid (NTA), ethylenediaminetetraacetic acid (EDTA), diethylenetriaminepentaacetic acid (DTPA), and iminodiacetic acid (IDA). Exemplary polyphosphonates include diethylenetriaminepenta (methylenephosphonic acid) (DTPPH), nitrilotris(methylenephosphonic acid) and (NTMP), and 1-hydroxyethane-1,1-diphosphonic acid (HEDP). Other exemplary metal chelators include N-(1,2- dicarboxyethyl)-D,L-aspartic acid (IDS, also known as iminodisuccinic acid), polyaspartic acid (DS), ethylenediamine-N,N'-disuccinic acid (EDDS), N,Nbis(carboxymethyl) glutamic acid (GLDA), and methylglycinediacetic acid (MGDA).

The sample buffer 60 may also comprise a process control. The process control preferably comprises a nucleic acid. The nucleic acid undergoes sample processing, serves as a template in amplification, and in so doing serves as a positive control in reaction wells (see below) in which primers specific for the nucleic acid are present and a negative control in reaction wells in which primers specific for the nucleic acid are not present. The nucleic acid may take the form of a purified nucleic acid or a nucleic acid encompassed within a cell or virion. Among nucleic acid encompassed within a cell or virion, the nucleic acid may be genomic DNA, plasmid DNA, mitochondrial DNA, genomic RNA, ribosomal RNA, messenger RNA, or any other type of nucleic acid harbored by a cell or virion. Accordingly, the process control may itself comprise purified nucleic acid, cell, or virion. The cell or virion may be fixed with formalin or other type of fixatives which are well known in the art. In some versions, the process control is provided in the body cavity 15 in dried form without sample buffer 60.

The sample buffer 60 may also comprise a reducing agent. The reducing agent is preferably included in an amount of from about 0.1 µM to about 300 µM, but amounts above and below these values are acceptable. Exemplary reducing agents include tris(2-carboxyethyl)phosphine (TCEP) and dithiothreitol (DTT).

The sample buffer 60 may also comprise an antimicrobial to prevent growth of contaminants. The antimicrobial may comprise an antibacterial, an antifungal, and/or an antiparasitic. Antibacterials include antibiotics, which are well known in the art. Exemplary antibiotics include penicillins, cephalosporins, polymyxins, rifamycins, quinolones, sulfonamides, macrolides, lincosamides, tetracyclines, cyclic lipopeptides (such as daptomycin), glycylcyclines (such as tigecycline), oxazolidinones (such as linezolid), and lipiarmycins (such as fidaxomicin). Exemplary antifungals include polyenes, imidazoles, triazoles, thiazoles, allylamines, and echinocandins. Exemplary antiparasitics include antinematodes, anticestodes, antitrematodes, antiamoebics, antiprotozoals. Exemplary antiprotozoals include melarsoprol, eflornithine, metronidazole, tinidazole, and miltefosine.

The sample buffer 60 may also comprise a non-enzymatic protein. Non-enzymatic proteins stabilize enzymes, increases nucleic acid amplification yields, and prevents adhesion of enzymes to surfaces. An exemplary non-enzymatic protein is bovine serum albumin (BSA) or other types of albumin.

Reaction Cartridge

Figure 6A:
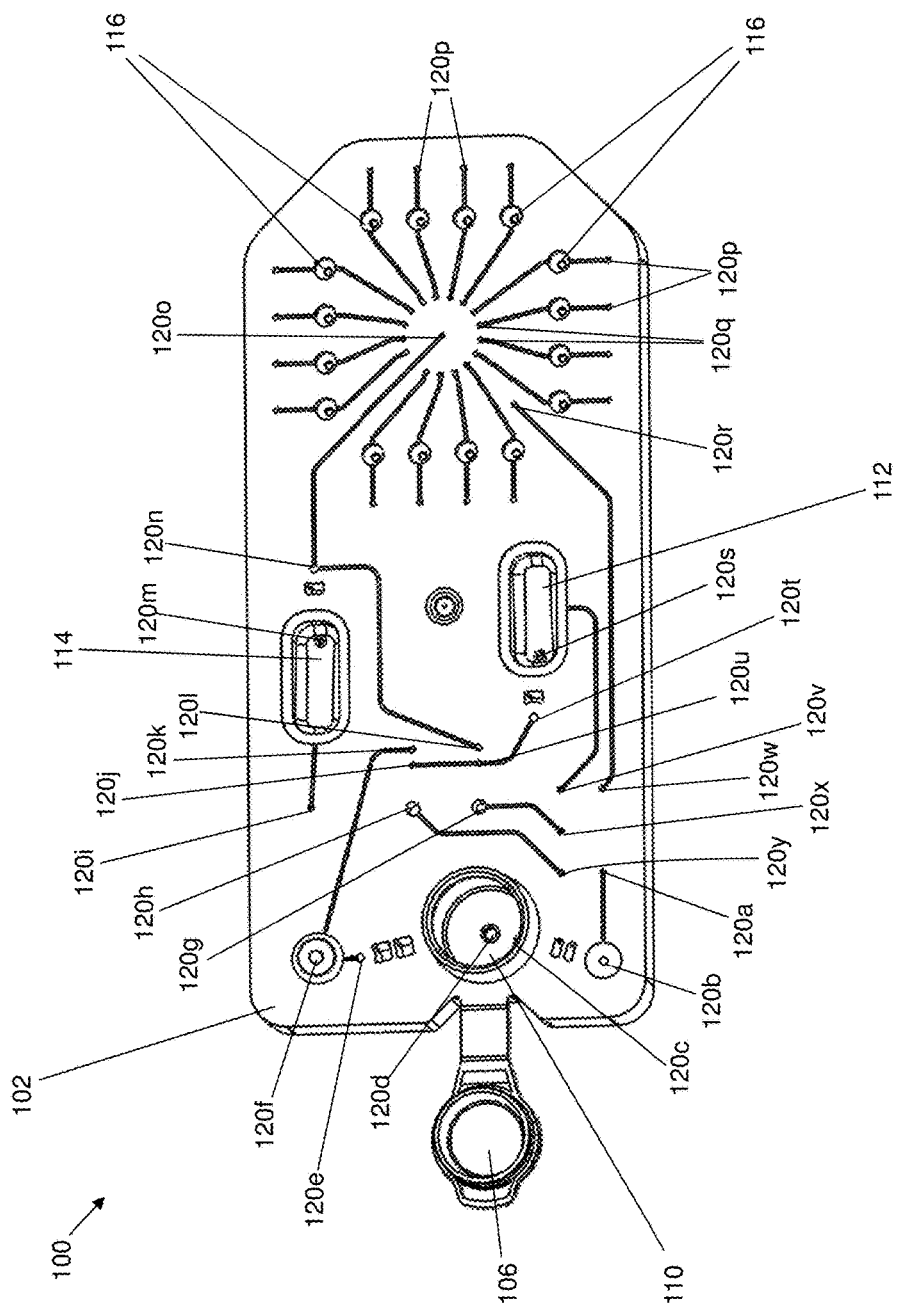
FIGS. 6A and 6B are top perspective views of a reaction cartridge plate of the invention.

FIGS. 6A-9B show various aspects of an exemplary reaction cartridge of the invention. The reaction cartridge comprises a reaction cartridge plate 100. A top view of the reaction cartridge plate 100 is shown in FIGS. 6A and 6B. A shown in FIG. 6A, a top side 102 of the reaction cartridge plate 100 defines a sample collection well 110, a sample mixing well 112, a master mix well 114, and 16 separate reaction wells 116. A cap 106 configured to seal the sample collection well 110 in a fluid-tight manner is attached to the reaction cartridge plate 100. A number of vertical channels 120a-120y span the reaction cartridge plate 100 from the top side 102 to the bottom side 104 of the reaction cartridge plate 100. Channel 120f is optionally fitted with a spear valve. As shown in FIG. 6B, a number of horizontal grooves 130a-130m are defined in the top side 102 of the reaction cartridge plate 100. Each groove 130a-130m connects one of the channels 120a-120y to another one of the channels 120a-120y or connects one of the channels 120a-120y to one of the sample collection well 110, the sample mixing well 112, the master mix well 114, or a reaction well 116. For example, groove 130a connects channel 120a with channel 120b, groove 130j connects channel 120v with the sample mixing well 112, groove 130d connects channel 120i to the master mix well 114, etc.

Figure 6B:
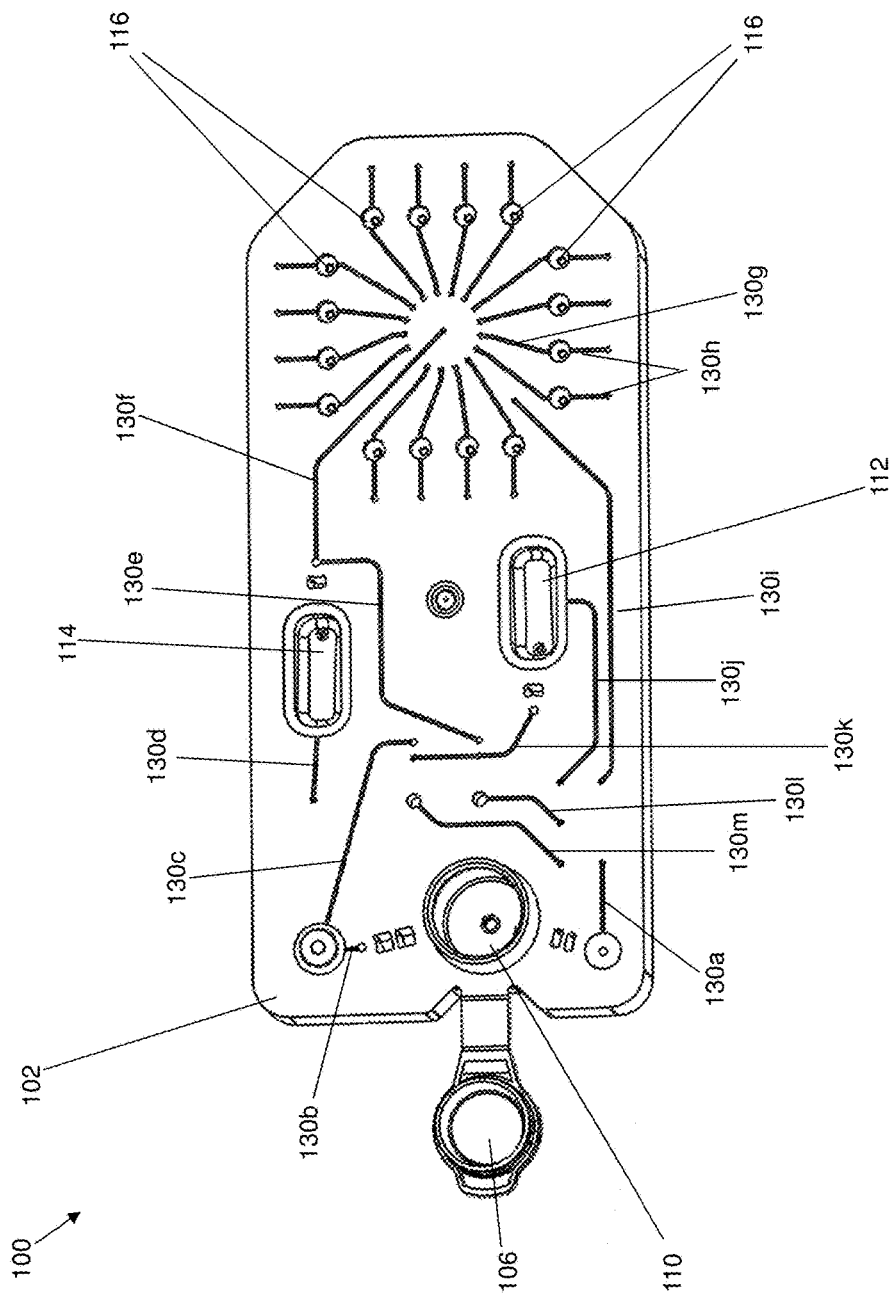
Figure 7A:
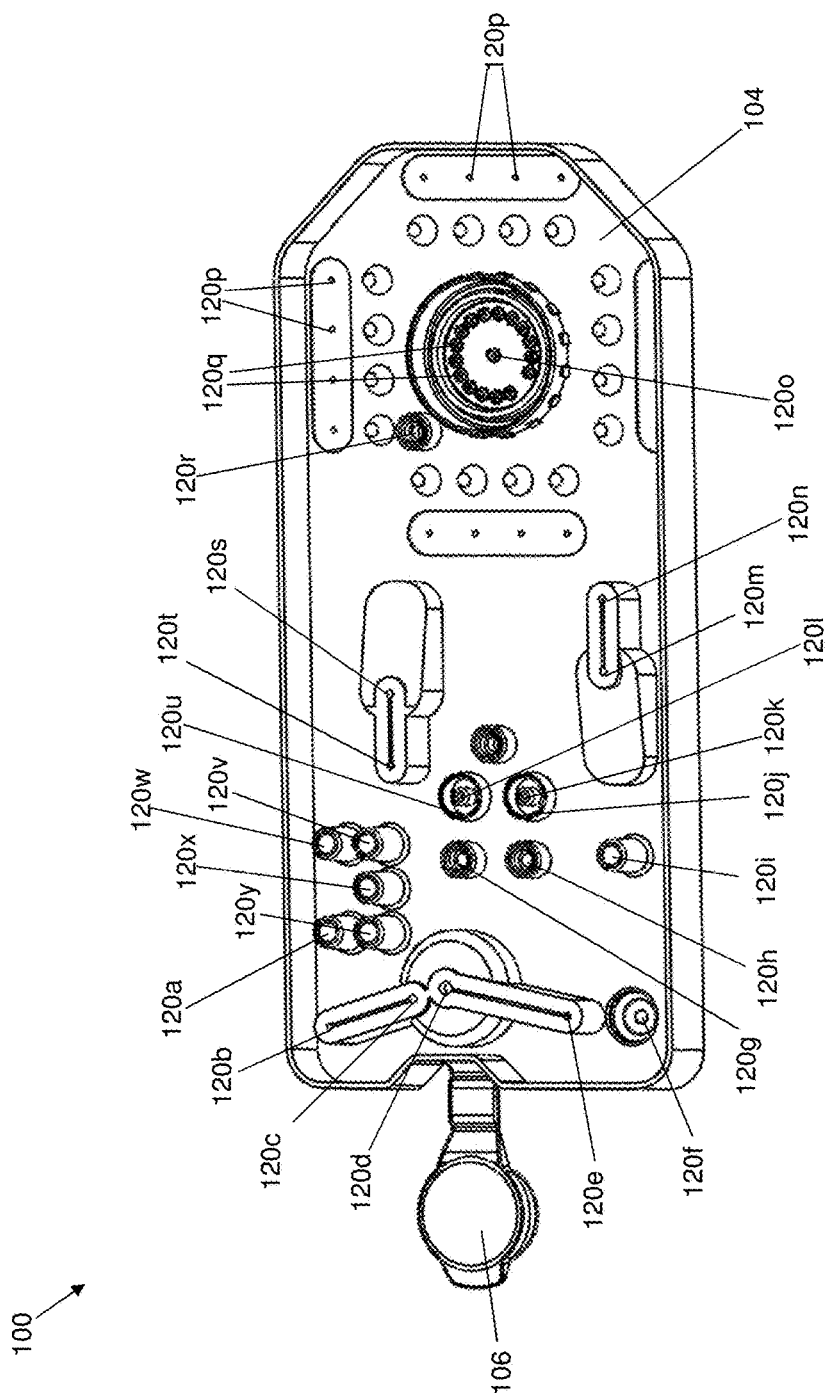
FIGS. 7A and 7B are bottom perspective views of a reaction cartridge plate of the invention.
Figure 7B:
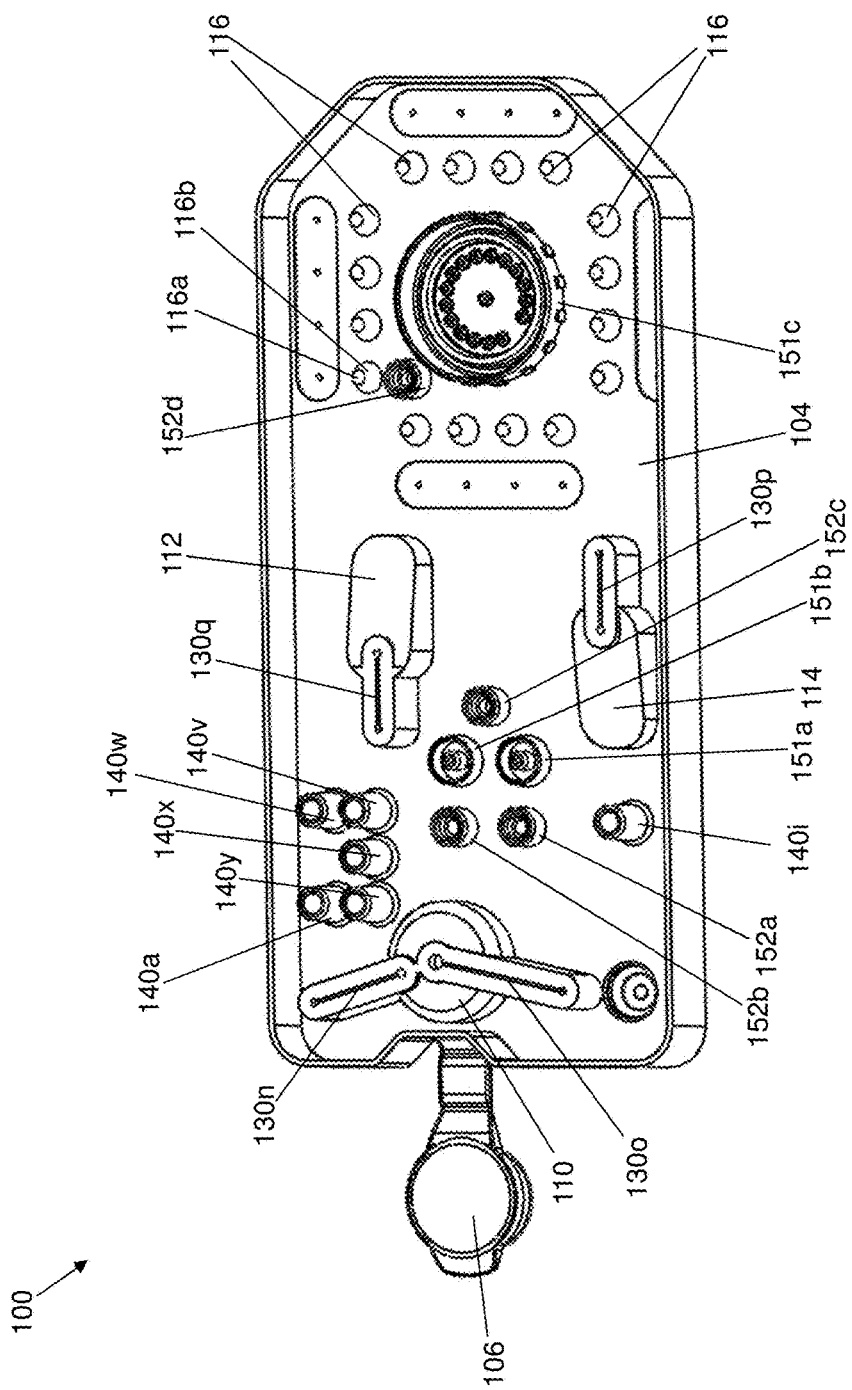

A bottom view of the reaction cartridge plate 100 is shown in FIGS. 6A and 6B. FIG. 7A depicts channels 120a-120y as they open to the bottom side 104 of the reaction cartridge plate 100. FIG. 7B shows the undersides of the sample collection well 110, the sample mixing well 112, the master mix well 114, and reaction wells 116. The bottoms and sides of the reaction wells 116 are preferably transparent to the wavelengths of light used to illuminate reaction content and optically detect reaction products, respectively. A separate air nozzle 140a,140y,140x,140w,140v,140i is defined about the openings of each of channel 120a, channel 120y, channel 120x, channel 120w, channel 120v, and channel 120i, respectively. The air nozzles 140a,140y,140x,140w,140v, 140i are configured to connect to pressure actuators, such as fluid (e.g., air) pumps. The bottom side 104 also includes three valve wells 151a,151b,151c. Valve well 151a is defined around and encompasses the openings to channel 120j and channel 120k. Valve well 151b is defined around and encompasses the openings to channel 120u and channel 120l. Valve well 151c is defined around and encompasses the openings to channel 120o and all of channels 120q. The bottom side 104 also includes four separate fittings 152a, 152b,152c,152d. Fitting 152a is defined around the opening to channel 120h. Fitting 152b is defined around the opening to channel 120g. Fitting 152d is defined around the opening to channel 120r. Finally, the bottom side 104 includes a number of grooves 130n-130q. Groove 130n connects the opening to channel 120b and the opening to channel 120c. Groove 130o connects the opening to channel 120d and the opening to channel 120e. Groove 130p connects the opening to channel 120m and the opening to channel 120n. Groove 130q connects the opening to channel 120s and the opening to channel 120t.

Figure 8A:
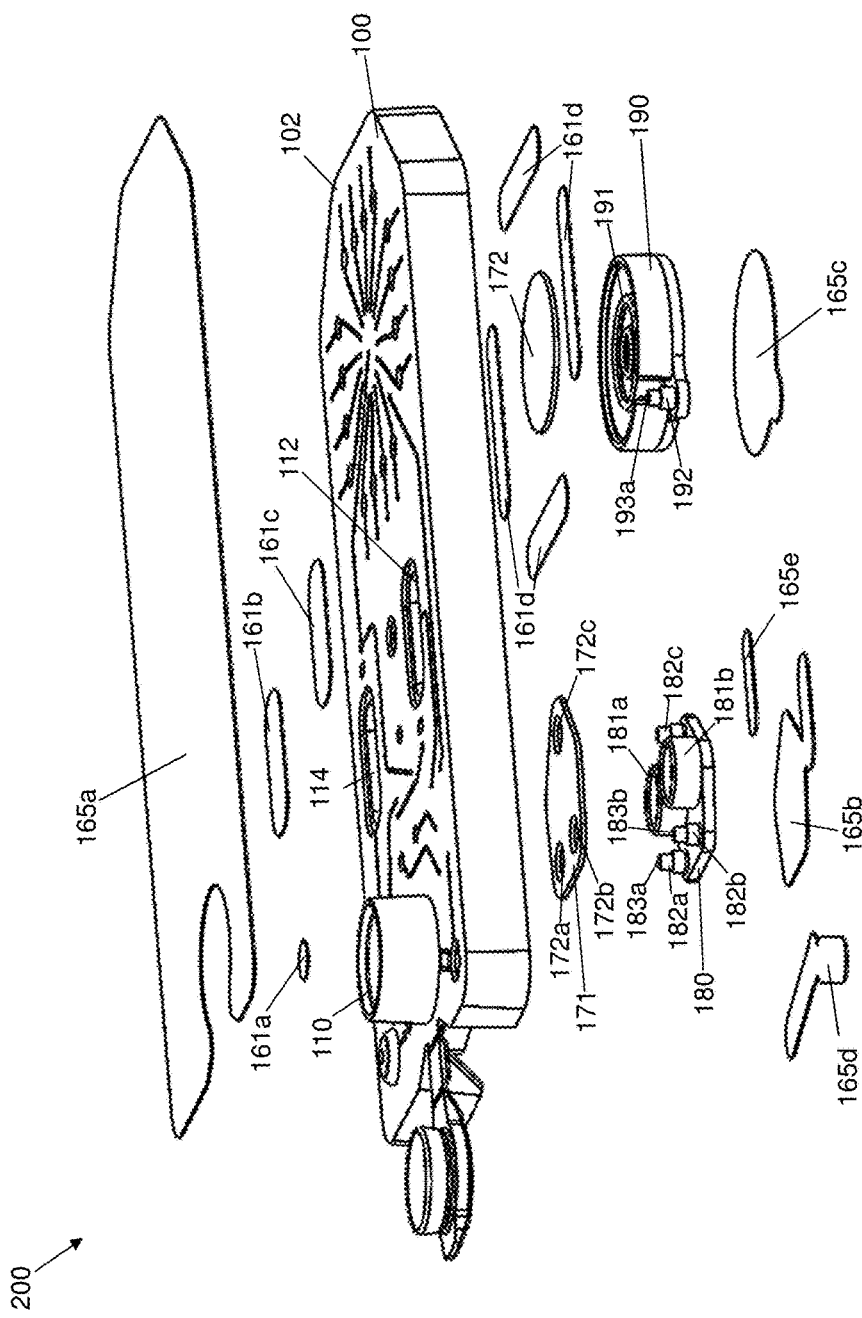
FIGS. 8A and 8B show a reaction cartridge of the invention.

Chambers, fluid channels, and valves are formed by placing silicone membranes, heat-seal films, and caps on the various elements of the top side 102 and the bottom side 104 of the reaction cartridge plate 100. As shown in FIG. 8A, a separate hydrophobic membrane 161a,161b,161c, such as polypropylene or polypropylene backed polytetrafluoroethylene, is placed over each of the opening to channel 120c in the sample collection well 110, the opening to channel 120m in the master mix well 114, and the opening to channel 120s in the sample mixing well 112, respectively. The hydrophobic membranes are permeable to air but not aqueous liquid and effectively form air vents. A liquid-proof heat seal film, such as a foil or polypropylene backed foil, 165a is then placed over the entire top side 102, with the exception of the sample collection well 110. Placing the heat seal film on the top side 102 forms a sample mixing chamber 212 (see FIG. 10A) from the sample mixing well 112, a master mix chamber 214 (see FIG. 10A) from the master mix well 114, and reaction chambers 216 from the reaction wells 116 (see FIG. 10A). Placing the heat seal film on the top side 102 also forms horizontal fluid channels from grooves 130a-130m.

Figure 8B:
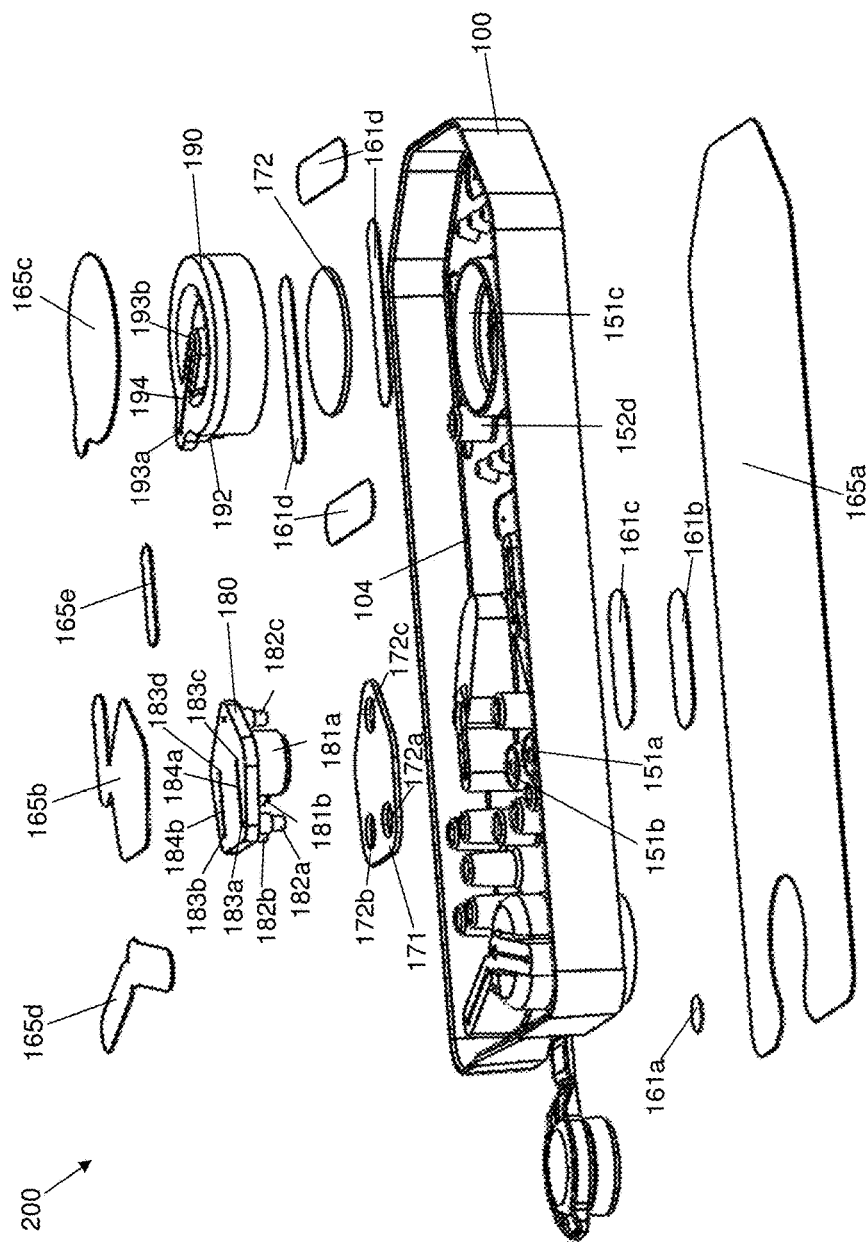

As shown in FIG. 8B, a silicon membrane 171 is placed over the openings of both valve well 151a and valve well 151*b*. Silicon membrane 171 has fitting cutouts 172*a*,172*b*, 172*c* to provide access to fittings 152*a*,152*b*,152*c*, respectively. A valve cap 180 is then placed over and through the silicon membrane 171. The valve cap 180 includes fitting inserts 182*a*,182*b*,182*c* configured to fit through the fitting cutouts 172*a*,172*b*,172*c* of the silicon membrane 171 and into fittings 152*a*,152*b*,152*c* on the bottom side 104 of the reaction cartridge plate 100. The valve cap 180 also includes two valve manifolds 181*a*,181*b* configured to abut the silicone membrane 171 in register with valve well 151*a* and valve well 151*b*, respectively. Four vertical channels 183*a*, 183*b*,183*c*,183*d* extend through the valve cap 180. Channel 183*a* extends through fitting insert 182*a* and forms a continuous channel with channel 120*h* when fitting insert 182*a* is inserted in fitting 152*a*. Channel 183*b* extends through fitting insert 182*b* and forms a continuous channel with channel 120*g* when fitting insert 182*b* is inserted in fitting 152*b*. Channel 183*c* extends into valve manifold 181*a*. Channel 183*d* extends into valve manifold 181*b*. Groove 184*a* connects channels 183*a* and 183*c*, and groove 184*b* connects channels 183*b* and 183*d*. Heat seal film 165*b* is placed over channels 183*a*,183*b*,183*c*,183*d* and grooves 184*a*,184*b* in the valve cap 180 to form fluid channels therewith. Heat seal film 165*b* also covers channel 120*t*, groove 130*q*, and channel 120*s* to form a fluid channel therewith.

A second silicon membrane 172 is placed over the opening of valve well 151*c*. A distribution valve cap 190 is then attached over the silicon membrane 172 and valve well 151*c*. The distribution valve cap 190 includes a fitting insert 192 (shown more clearly in FIG. 8A) configured to fit into fitting 152*d*. The distribution valve cap 190 also includes a valve manifold 191 (shown in FIG. 8A) configured to abut the silicone membrane 172. Two channels 193*a*,193*b* extend through the distribution valve cap 190. Channel 193*a* extends through fitting insert 192 and forms a continuous channel with channel 120*r* when fitting insert 192 is inserted in fitting 152*d*. Channel 193*b* extends into valve manifold 191. Groove 194 connects channel 193*a* and channel 193*b*. Heat seal film 165*c* is placed over channels 193*a*,193*b* and groove 194 to form a horizontal fluid channel therewith.

To form additional fluid channels, heat seal film 165*d* is placed over channels 120*b*,120*c* and groove 130*n* and also over channels 120*d*,120*e* and groove 130*o*. Heat seal film 165*e* is placed over channels 120*m*,120*n* and groove 130*p*. To provide liquid-proof air vents for the reaction chambers 216, hydrophobic membranes 161*d* are placed over the openings to channels 120*p* on the bottom side 104 of the reaction cartridge plate 100.

Figure 9:
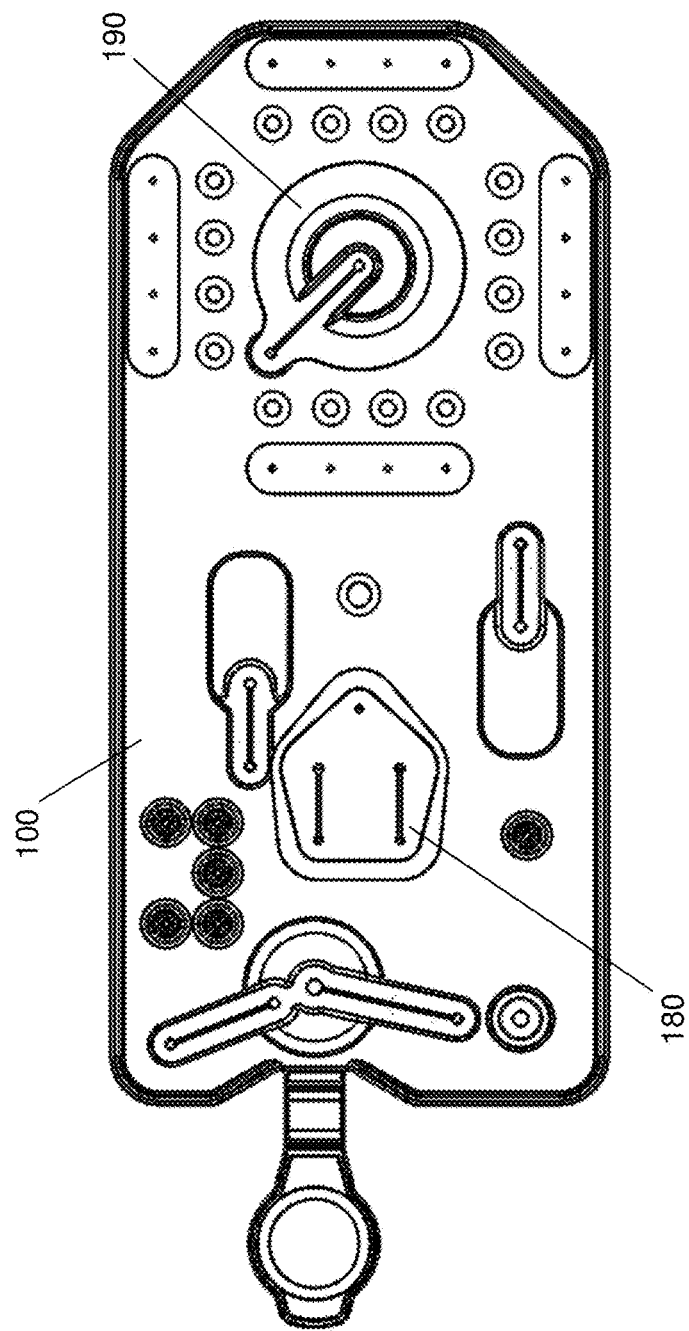
FIG. 9 is a bottom plan view of a reaction cartridge plate of the invention with a valve cap and a distribution cap attached thereto, showing grooves defined thereon.

A bottom plan view of the bottom side 104 of the reaction cartridge plate 100 with the valve cap 180 and the distribution cap 190 attached thereto is shown in FIG. 9. The channels that would be formed on the bottom 104 of the reaction cartridge plate 100 from attaching heat seal films 165*b*,165*c*,165*d*,165*e* are visible in this view.

Figure 10A:
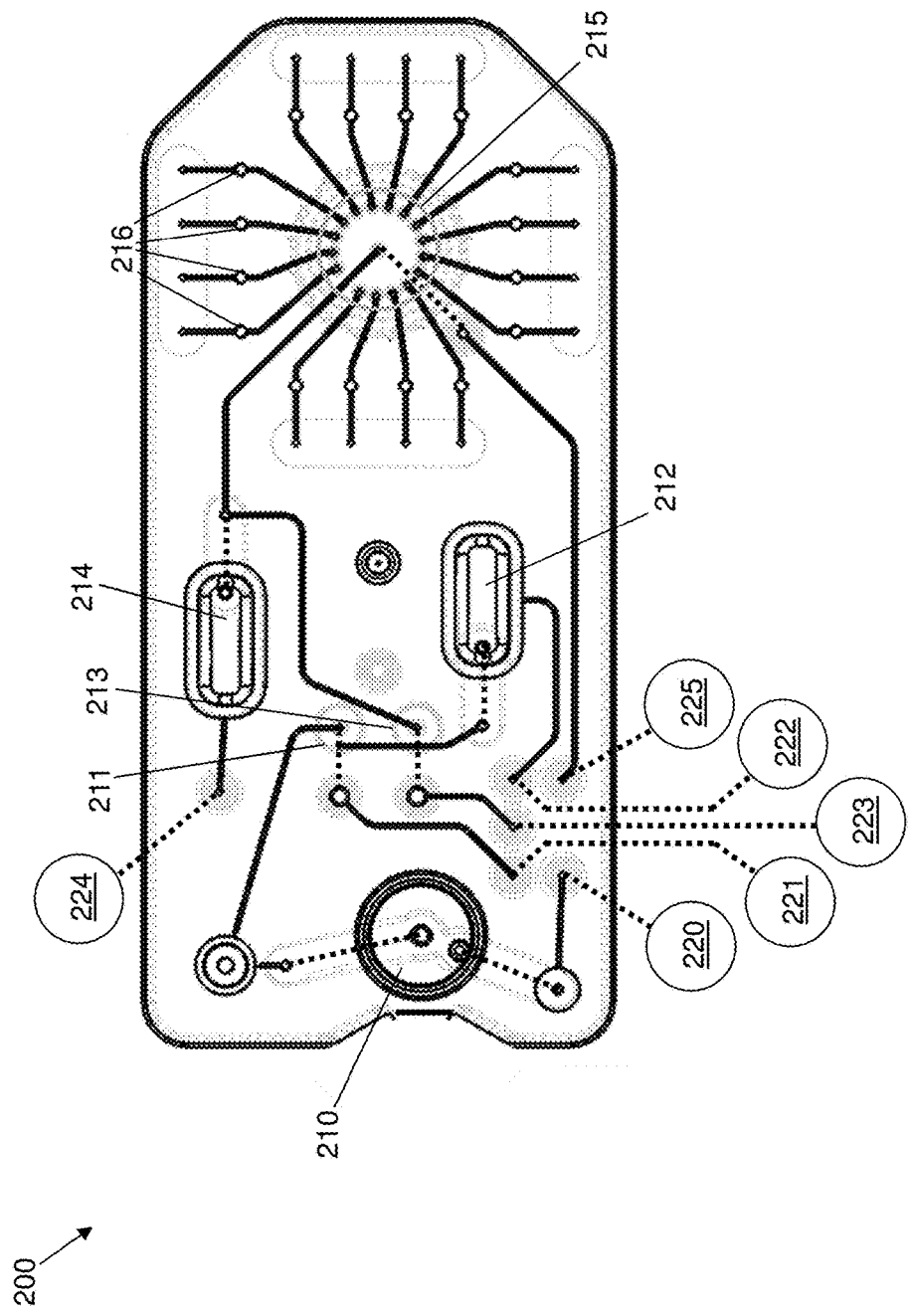
FIG. 10A is a top plan schematic of a reaction cartridge of the invention attached to pressure actuators. Fluid channels spanning the top of the reaction cartridge are shown as solid lines. Fluid channels spanning the bottom of the reaction cartridge are shown as dashed lines. Select elements on the bottom side of the reaction cartridge are shown in phantom view.

Forming the chambers, fluid channels, and valves on the reaction cartridge plate 100 as described above results in a reaction cartridge 200 as shown in FIG. 10A. The reaction cartridge 200 includes a sample collection chamber 210, a sample mixing chamber 212, a master mix chamber 214, and multiple reaction chambers 216. The sample collection chamber 210 is formed when the cap 106 is closed on the sample collection well 110. The sample mixing chamber is formed from the hydrophobic membrane 161*c* placed at the bottom of the sample mixing well 112 and the heat seal film 165*a* placed over the sample mixing well 112. The master mix chamber 214 is formed from the hydrophobic membrane 161*b* placed at the bottom of the master mix well 114 and the heat seal film 165*a* placed over the master mix well 114. The reaction chambers 216 are formed from the heat seal film 165 placed over the reaction wells 116.

The reaction cartridge 200 also includes a first valve 211, a second valve 213, and a third valve 215. The first valve 211 is formed from valve manifold 181*a*, silicon membrane 171, and valve well 151*a* when the valve cap 180 is attached to the reaction cartridge plate 100. The second valve 213 is formed from valve manifold 181*b*, silicon membrane 171, and valve well 151*b* when the valve cap 180 is attached to the reaction cartridge plate 100. The third valve 215 is a distribution valve formed from valve manifold 191, silicon membrane 172, and valve well 151*c* when the distribution valve cap 190 is attached to the reaction cartridge plate 100.

The connectivities among the chambers and valves are provided by the fluid channels formed as described above. The solid lines in FIG. 10A depict the fluid channels running along the top side 102 of the reaction cartridge plate 100, and the dashed lines depict the channels running along the bottom side 104 of the reaction cartridge plate.

Figure 10B:
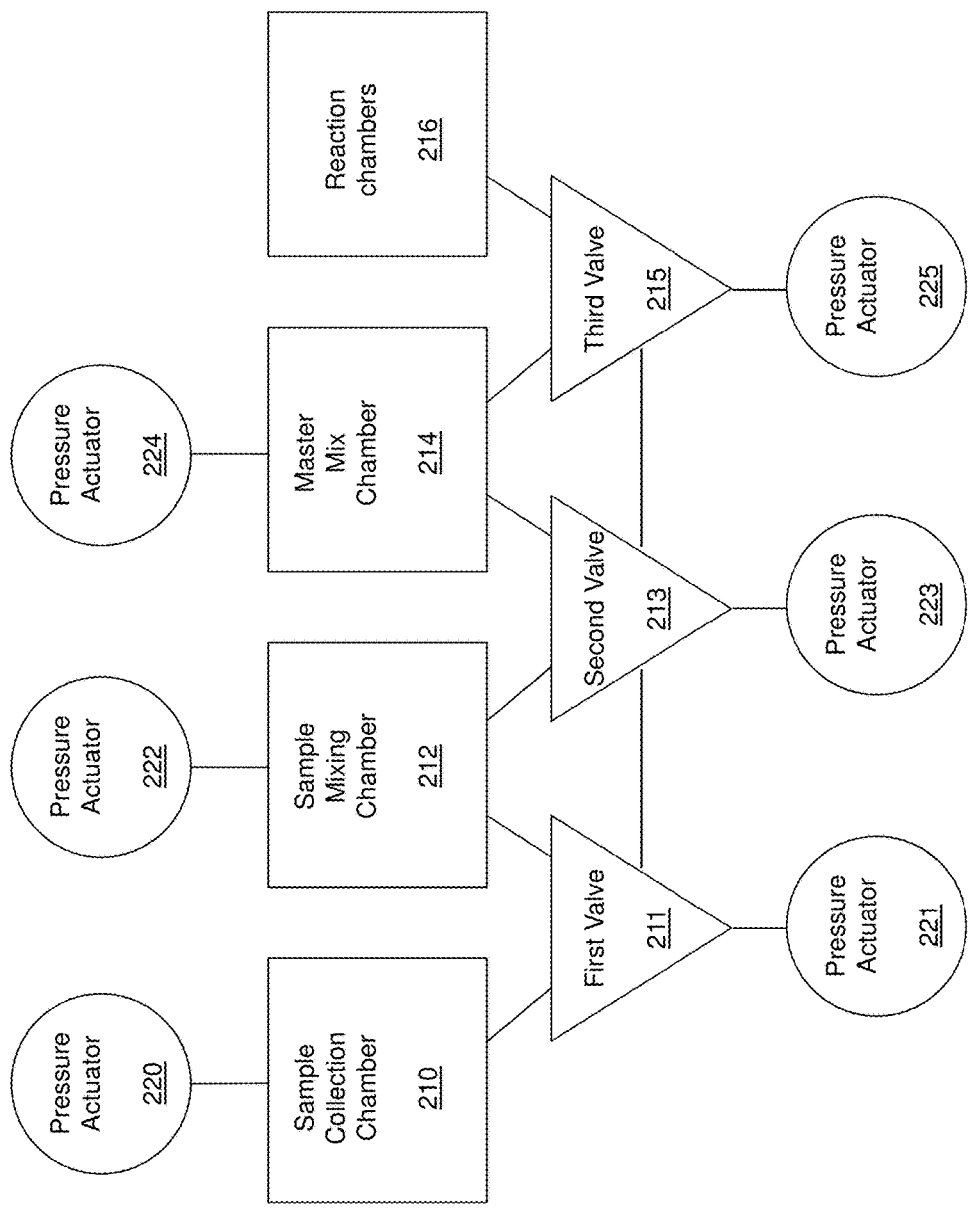
FIG. 10B is a schematic showing the connectivities of the various elements of the reaction cartridge and associated devices of the invention. Squares represent chambers of the reaction cartridge. Triangles represent valves of the reaction cartridge. Circles represent pressure actuators attached to the reaction cartridge. Lines represent fluid-transfer connectivities among the elements.

A schematic showing the fluid connectivities of the elements of the reaction cartridge 200 is shown in FIG. 10B. The first valve 211 is in direct fluid communication with the sample collection chamber 210, the sample mixing chamber 212, and the second valve 213. The second valve 213 is in direct fluid communication with the first valve 211, the sample mixing chamber 212, the master mix chamber 214, and the third valve 215. The Third valve is in direct fluid communication with the second valve 213, the master mix chamber 214, and the reaction chambers 216. The sample collection chamber 210, the sample mixing chamber 212, the master mix chamber 214, and the reaction chambers 216 are not in direct fluid communication with each other and are connected only via the valves 211,213,215.

The valves 211,213,215 are actuated with pressure, such as air pressure. In the exemplary version of the invention provided herein, the valves 211,213,215 close by being pressurized with air and open by releasing the pressure. Pressure actuators 221,223,225, such as air pumps can be placed in fluid communication with valves 211,213,215 via air nozzles 140*y*,140*x*,140*w*, respectively, and can actuate the pressurization. The pressure actuators 221,223,225 may also actively release pressure in the valves 211,213,215. Alternatively, the valves 211,213,215 may be configured to passively release pressure by venting. The exemplary valves 211,213,215 are non-selectable valves, wherein the valves 211,213,215 prevent flow therethrough to all directly connected channels when off and permit flow to all directly connected channels when on. Directional valves, which selectively direct fluid flow to a subset of the connected channels is within the scope of the present invention.

The movement of liquid throughout the system is also actuated with pressure, such as air pressure. In the exemplary version of the invention provided herein, liquid moves from chamber to chamber by pressurizing the chambers from which liquid is to be moved and, optionally, actively releasing pressure in chambers to which the liquid is to be moved. Pressure actuators 220,222,224, such as air pumps, can be placed in fluid communication with the sample collection chamber 210, the sample mixing chamber 212, and the master mix chamber 214 via air nozzles 140*a*,140*v*, 140*i*, respectively, and can actuate the pressurization and optional release of pressure in the valves. In other versions, the chambers can be vented and passively release the pressure upon withdrawal of pressurization.

The reaction cartridge 200 is preferably configured as a disposable, single-use plastic device. The reaction cartridge plate 100 is preferably made of polymeric material such as polypropylene. In some versions, the reaction cartridge 200 is no larger than 20 cm, no wider than 10 cm, and has a depth no larger than 3 cm. The thickness of the plastic in the reaction cartridge plate 100 is preferably between 0.1 mm to 2 mm for optimal thermal conductance and optimal light detection. Parameters of the reaction cartridge 200 outside of these ranges are encompassed by the invention.

Each the sample mixing chamber 212, the master mix chamber 214, and the reaction chambers 216 may include reagents for performing functions in the immediate or downstream chambers. The reagents may be included in dried form. The reagents may be air dried in situ, or added as lyophilized beads.

The sample mixing chamber 212 is preferably configured for releasing and/or exposing nucleic acid for downstream amplification. The releasing or exposing of nucleic acid may comprise lysis of cells or viruses by heating or exposure to lysis reagents. Examples of lysis reagents include detergents, cell-wall lysis enzymes, and reducing reagents. The lysis reagents are preferably included in an amount sufficient for sample lysis without inhibiting downstream amplification. The detergent may be nonionic, ionic, or zwitterionic, but nonionic and zwitterionic detergents are preferred. Exemplary detergents include Triton X-100, Triton X-114, NP-40, Brij-35, Brij-58, Tween 20, Tween 80, octyl glucoside, octyl thioglucoside, sodium dodecyl sulfate (SDS), 3-[(3-cholamidopropyl)dimethylammonio]-1-propanesulfonate (CHAPS), and 3-[(3-cholamidopropyl)dimethylammonio]-2-hydroxy-1-propanesulfonate (CHAPSO). Exemplary cell-wall lysis enzymes include peptidoglycan lyase, β-N-acetylmuramidase, β-1,3-glucanase. Commercial cell-wall lysis enzymes include Yatalase (Clontech, Mountain View, Calif.), Zymolase (Zymo Research, Irvine, Calif.) and CellLytic Y (Sigma-Aldrich). Exemplary reducing reagents are described elsewhere herein.

The sample mixing chamber 212 may also comprise any reagent described below as being included in the master mix chamber 214 and the reaction chambers 216. In preferred versions, however, the sample mixing chamber 212 is devoid or substantially devoid of a DNA polymerase for the purpose of avoiding premature denaturation of the enzyme and is also devoid or substantially devoid of primers for the purpose of providing specificity in at least a subset of the reaction chambers 216. The sample mixing chamber 212 may also comprise non-enzymatic protein, metal chelators, and resin particles. Exemplary resin particles include ion exchange resins and gel filtration resins.

The master mix chamber 214 is preferably configured for adding non-specific amplification reagents to the lysed sample for even distribution in the sample which is ultimately divided among the reaction chambers 216. Non-specific amplification reagents may include a magnesium salt, an ammonium or potassium salt, deoxynucleotide triphosphates, sugars, non-enzymatic protein, and a DNA polymerase. The amplification reagents are preferably included in an amount such that, when reconstituted with the sample, are provided to the reaction chambers 216 in a concentration to facilitate nucleic acid amplification. Exemplary magnesium salts include magnesium sulfate and magnesium chloride. Exemplary ammonium or potassium salts include ammonium sulfate and potassium chloride. Exemplary deoxynucleotide triphosphates (dNTPs) include deoxyadenosine triphosphate (dATP), deoxyguanosine triphosphate (dGTP), deoxythymidine triphosphate (dTTP), deoxyuridine triphosphate (dUTP), deoxycytidine triphosphate (dCTP), deoxyinosine triphosphate (dITP), and deoxyxanthosine triphosphate (dXTP). Exemplary sugars include trehalose, sucrose, manitol, and sorbitol.

The DNA polymerase preferably comprises at least a DNA-dependent DNA transcriptase. For use with RNA analytes, the DNA polymerase preferably further comprises a reverse transcriptase (RNA-dependent DNA polymerase). In some cases, the DNA polymerase may comprise a single enzyme having both DNA-dependent DNA polymerase activity and reverse transcriptase activity. Examples of enzymes having both reverse transcriptase and DNA-dependent polymerase activity include the 3173 Exonuclease Minus (Exo-) DNA Polymerase from Lucigen Corporation (Madison Wis.), the Bst 2.0 DNA Polymerase from New England BioLabs Inc. (Ipswich, Mass.), and the GspSSD LF DNA Polymerase from OptiGene (West Sussex, UK), among others. Further examples include the polymerases and sequence variants thereof described in US 2012/0083018 (U.S. application Ser. No. 13/313,783), which is incorporated herein by reference. The master mix chamber 214 preferably comprises at least a DNA polymerase.

The master mix chamber 214 may also comprise any reagent described above as being included in the sample mixing chamber 212 and any reagent described below as being included in the reaction chambers 216. In preferred versions, however, the master mix chamber 214 is devoid or substantially devoid of primers for the purpose of providing specificity in at least a subset of the reaction chambers 216. The master mix chamber 214 may also comprise a DNA detection reagent.

The reaction chambers 216 are preferably configured for amplifying and detecting nucleic acid. In cases in which different specific amplification reactions are not required among different reaction chambers 216 or in which there is only one reaction chamber 216, the reaction chamber(s) 216 may comprise any or all of the non-specific amplification reagents described above for the master mix chamber 214 in addition to primers. In such cases, the master mix chamber 214 may be devoid or substantially devoid of these reagents or be omitted altogether. In cases in which different specific amplification reactions are desired among the different reaction chambers 216, the reaction chambers 216 may comprise primers without the non-specific amplification reagents, as the non-specific amplification reagents are provided with incoming sample from the master mix chamber 214. The primers in the reaction chambers 216 may be specific to different analyte targets, such that different amplification reactions are capable of being conducted in different reaction chambers 216. The primers are preferably present in a combination and an amount sufficient to generate a DNA copy of any present RNA template and to amplify the DNA copy into a detectable amount. The design of primers for reverse transcription and amplification, including isothermal amplification, is well-known in the art.

For detection of amplified nucleic acid, the reaction chambers 216 also preferably comprise a DNA detection reagent. The DNA detection reagent is preferably provided in an amount to indicate the presence of amplified DNA. Exemplary DNA detection reagents include double-stranded DNA detection reagents and sequence-specific probes (hybridization probes). Double-stranded DNA detection reagents are well known in the art. Exemplary double-stranded DNA binding reagents include PICOGREEN (Life Technologies, Carlsbad, Calif.), SYBR Green (Life Technologies), ethidium bromide, and FIONAGREEN (Marker Gene Technologies, Inc., Eugene, Oreg.), among others.

Exemplary sequence-specific probes include fluorophore-labeled probes and radiolabeled probes. Exemplary sequence-specific probes include SCORPIONS probes (Sigma-Aldrich, St. Louis, Mo.), molecular beacon probes, TAQMAN probes (Roche Molecular Diagnostics, Basel, Switzerland), Molecular Beacon probes, and LNA (Locked Nucleic Acid) probes, among others. The use of sequence-specific probes with the present invention may require DNA melting and annealing steps. Alternatively, the amplification product can be detected using a lateral flow detection device designed to provide a visual indication of the presence of a specific amplification product.

The reaction chambers 216 may also comprise any reagent described above as being included in the sample mixing chamber 212 and the master mix chamber 214.

In some versions of the invention, the sample collection chamber 210 is configured to accommodate up to 3 ml of liquid, and the sample mixing chamber 212 and the master mix chamber 214 are each configured to accommodate up to 1 ml of liquid. Volume capacities above and below these volumes are encompassed by the invention.

The fluid channels in the reaction cartridge 200 preferably have diameters in the range from 0.2 mm to 2 mm. The air nozzles 140a,140y,140x,140w,140v,140i are preferably configured to carry in air pressurized up to 20 lb./sq. inch. Parameters outside of these ranges are encompassed by the invention.

Each reaction well 116 preferably comprises at least two optically transparent windows, an excitation wall 116a for illuminating the reaction content and a light emission/detection wall 116b for detecting fluorescence. See FIG. 7B. The light emission/detection wall 116b is preferably angularly offset from the excitation wall 116a to minimize exciting light entering detection window and also to maximize the amount of emitted light signal by maximizing the length of fluid path sampled. It is preferred that the angular offset is between 0° and 90°. It is preferred that the excitation wall 116a comprises a flat bottom portion of the reaction well 116 and that the emission/detection wall 116b comprises an angular side wall of the reaction well 116. With this configuration, each reaction 116 well is preferably illuminated from the bottom of the well and the emitted fluorescence signal is detected from the side of the well. The light illumination path and the light detection path are preferably at an angle of less than 90 degrees. The illuminating light source and optical detector are preferably provided in a separate instrument bay.

The reaction cartridge 200 can be configured to be matingly placed on a corresponding cartridge reader for use therewith. The cartridge reader may comprise the pressure actuators 220-225 (e.g., air pumps or other fluid pumps) that connect to the reaction cartridge, heating elements for heating various chambers, e.g., 212,214,216, and a light emitter (excitation light source) and a light detector (optical sensor) for detecting reaction products in the reaction chambers 216. The cartridge reader may further comprise a circuit board, a microprocessor, a cooling fan, and a bar code reader. The cartridge reader includes or is connected to a power supply for powering. The cartridge reader is preferably controlled by an on-board computer. The computer is programmed to perform the various functions needed to run the assay, analyze data, and provide an output in the form of screen display, print out, or both. The bar code reader scans bar codes affixed to the sample collection module 1 and/or the reaction cartridge 200 for information such as the assay type, reagent lot number, part expiry date, and protocols for the processing of the reaction cartridge 200. The shape of the reaction cartridge 200, including various notches and protrusions, may serve to align the reaction cartridge 200 with the cartridge reader.

An exemplary use of the reaction cartridge 200 is for amplifying nucleic acid such as DNA in a sample for detection thereof. A sample is introduced into the sample collection well 110, such as with the sample collection module 1 described above. The cap 106 is closed, thereby sealing the sample in liquid form in the sample collection chamber 210. A predetermined volume of sample is then transferred from the sample collection chamber 210 to the sample mixing chamber 212 by pressurizing the sample collection chamber 210 while opening the first valve 211 and closing the second valve 213. Opening the first valve 211 permits movement of the sample from the sample collection chamber 210 to the sample mixing chamber 212, and closing the second valve 213 prevents movement of the sample to the master mix chamber 213, the third valve 215, and the reaction chambers 216. The volume of sample transferred to the sample mixing chamber 212 may be metered by the duration of pressure applied in the sample collection chamber 210, by measuring the back pressure once the sample mixing chamber 212 is full, or a combination thereof.

Once in the sample mixing chamber 212, the sample is heated for cell lysis and release of nucleic acids. The sample mixing chamber 212 preferably contains reagents to help cell lysis and subsequent nucleic acid amplification, as described elsewhere herein. The sample is preferably heated to a predetermined temperature through heating elements that contact the base of the sample mixing chamber 212 and is held at that temperature for a certain duration for optimal lysis and reagent dissolution. Following lysis, the sample is cooled down to a set temperature. The cooling may be performed by blowing air using an electric fan on the sample mixing chamber 212.

Upon completion of heat treatments in sample mixing chamber 212, the sample is moved into the master mix chamber 214 by pressurizing the sample mixing chamber 212 while closing the first valve 211, opening the second valve 213, and closing the third valve 215. Closing the first valve 211 prevents the sample from moving back to the sample collection chamber 210, and closing the third valve 215 prevents the sample from proceeding into the reaction chambers 216. The entire volume of sample is preferably transferred into the master mix chamber 214. Complete transfer is assured by timed transfer, measurement of back pressure once master mix chamber 214 is full, or a combination thereof. The master mix chamber 214 preferably contains reagents needed for nucleic acid amplification, such as deoxynucleotide triphosphates, $MgCl_2$ etc., and is heated by another heating element in the cartridge reader.

The sample may optionally be moved from the master mix chamber 214 back to sample mixing chamber 212 by pressurizing the master mix chamber 214 while closing the first valve 211, opening the second valve 213, and closing the third valve 215. Sample may be moved back and forth between the sample mixing chamber 212 and the master mix chamber 214 more than once for thorough mixing of all reagents. Upon complete mixing, the sample is returned to master mix chamber 214.

The reaction mixture is then moved from the master mix chamber 214 to the reaction chambers 215 by pressurizing the master mix chamber 214 while closing the second valve 213 and opening the third valve 215. The reaction chambers 215 may contain DNA primers specific to certain RNA/DNA targets, polymerases (e.g., RNA-dependent DNA polymerases, RNA-dependent DNA polymerases), fluorescent dye for DNA detection, and other assay components. DNA amplification reactions can then proceed in the reaction chambers 215. Amplification products can be detected by detecting a level of fluorescence from each well.

In some versions of the invention, different analyte detection assays are carried out in parallel in the different reaction chambers 216. In some versions, at least one of the assays measures the presence of a target analyte while at least a second assay measures a control analyte that has been introduced into the sample as a process control to verify that appropriate sample processing and reaction conditions were achieved. In some versions, a plurality of different tests may be carried out to detect the presence of more than one analyte in a single sample. These different analytes may be different strains of the same species or different species of pathogens all together. Carrying out different analyte detection assays can be performed by loading the different reaction chambers 216 with different dry reagents, such as different sets of primers. In this manner, a single reaction mixture can be distributed to the different reaction chambers 216, and the multitude of different reactions can occur in parallel.

Example 1: Detection of *Clostridium difficile* in Stool

The sample collection module 1 is prefilled with 2.5 ml of Tris-EDTA buffer. The Tris-EDTA buffer may contain a cell such as formalin-fixed *Staphylococcus aureus* bacteria as an internal process control. The *S. aureus* bacterial cells go through the various steps of sample processing, nucleic acid amplification, and nucleic acid detection. Positive detection of the *S. aureus* ensures the effectiveness the method steps and reagent integrity.

A presumptive *C. difficile*-positive stool specimen is sampled by inserting a ribbed end of a sample pick (pick) into the specimen, covering only the ribbed part of the pick. The sample is then introduced into the sample collection module 1 by opening the cap 20 and inserting the specimen-laden pick, ribbed end first, into the buffer in the sample collection module 1, breaking off the pick at a score line, leaving the lower half of the pick in the sample collection module 1, and closing the cap 20. The sample collection module 1 is then inverted, and its entire liquid content (about 2.5 ml of buffered sample) is emptied into the sample collection well 110 of the reaction cartridge 200. The process of inverting sample collection module 1 and squeezing the sample fluid through its nozzle 26 results in mixing and filtering of the diluted specimen in a single step.

Once the buffered sample is introduced into the sample collection well 110, the cap 106 is closed. A barcode affixed to a "skirt" of the cartridge is then scanned using the scanner of an instrument that identifies the test type (for example, detection of *Clostridium difficile* in stool specimen) and loads appropriate run parameters to drive fluidics, thermal, optics, and analysis components. The cartridge is then placed inside the instrument, a lid is closed, and a run is initiated.

Using an onboard automated process, the sample is moved from the sample collection chamber 210, through the first valve 211, and into the sample mixing chamber 212. The sample mixing chamber 212 contains a dried reducing agent, such as TCEP, and a cell-wall lysis enzyme, such as peptidoglycan lyase, β-N-acetylmuramidase, β-1,3-glucanase, etc. These components help in cell lysis. The sample is heated to about 80° C. in the sample mixing chamber 212 and held at about 80° C. for about 5 minutes. As the sample is heated, the TCEP is dissolved and mixed. The heating aids in cell lysis, inactivation of pathogens, and inactivation of various contaminating enzymes such as proteases and nucleases.

Following heat treatment, the sample is cooled to about 68° C. and then moved to the master mix chamber 214, where it mixes with additional dried reagents. The dried reagents in the master mix chamber 214 include a thermostable DNA polymerase capable of isothermal DNA amplification, magnesium sulfate, potassium chloride, dNTPs, and trehalose. Upon rehydration, the reagents reach concentration optimum to support DNA amplification.

The sample with the master mix is then transferred back and forth between the master mix chamber 214 and the sample mixing chamber 212 to mix the reagents before transferring to the reaction chambers 216. Alternatively, the sample with the master mix is directly transferred to the reaction chambers 216. Isothermal DNA amplification reactions are carried out in the reaction chambers 216 at a constant temperature and an optical signal is gathered in real time. Each reaction well contains primers suitable for specifically amplifying DNA from a particular target cell and a DNA detection reagent such as a DNA binding dye to optically detect amplified DNA in real time. For detecting *C. difficile*, at least one of the reaction chambers 216 contains a set of 6 LAMP DNA primers configured to specifically amplify a toxin gene segment from *C. difficile*. A second reaction chamber 216 contains a set of 6 LAMP primers specific for the amplification of a house keeping gene from *S. aureus*, the internal process control that was spiked in the sample collection module 1 buffer.

At the end of a preset reaction time, for example 30 min, optical signal from each reaction well is analyzed to generate positive and negative calls.

Example 2: Multi-Target Detection

The reaction cartridge 200 may be configured for detecting a plurality of targets, such as different types of bacteria, fungi, protozoa, and/or viruses, etc. In such a configuration, at least some of the 16 reaction wells 116 contain different sets of primers for detecting different targets. The primers may be specific to the *S. aureus* internal process control, target bacteria (e.g., *Clostridium difficile, Escherichia coli* O157, *Salmonella typhimurium, Yersinia enterocolitica, Vibrio cholera*), target viruses (e.g., norovirus GI/GII and rotavirus A), and target protozoa (e.g., *Entamoeba histolytica* and *Giardia lamblia*). The sample may contain one, some, or none of the targets. Presence or absence of each target pathogen is determined independently and in parallel with the capability of detecting up to 15 or more (if more than 16 reaction wells 116 are included) pathogens in addition to a process control in a single run.

Detection of Target RNA

The reaction cartridge 200 may be configured for detecting RNA from targets. The RNA may be genomic RNA (for targets having RNA genomes such as influenza virus) or may be other types of RNA harbored by the target, such as messenger RNA (mRNA), transfer RNA (tRNA), short nuclear RNA (snRNA) and ribosomal RNA (rRNA). A reaction cartridge 200 configured for detecting RNA may contain a reverse transcriptase in addition to a DNA-dependent DNA polymerase in the master mix chamber 214 and/or may contain a DNA polymerase having both reverse transcriptase and DNA-dependent polymerase activity. The reverse transcriptase activity creates a DNA template from the RNA target which in turn is amplified by the DNA-dependent DNA polymerase activity. An advantage of the enzymes having both reverse transcriptase and DNA-dependent polymerase activity is that both RNA and DNA targets can be detected with the same enzyme.

REFERENCES

The following references are all incorporated by reference in their entirety: U.S. Pat. Nos. 4,918,025; 4,806,316; 4,857,274; 4,963,498; 4,902,624; 4,940,527; 5,104,813; 5,133,937; 5,244,630; 5,147,606; 5,143,084; 5,374,522; 5,223,219; 5,229,297; 5,399,486; 5,605,662; 5,627,041; 5,498,392; 5,798,215; 6,004,512; 5,856,174; 5,922,591; 5,955,351; 5,882,903; 5,976,824; 5,863,502; 5,958,349; 5,948,673; 5,746,978; 6,168,948; 6,043,080; 6,197,595; 6,440,725; 6,440,725; 6,818,185; 6,818,185; 6,565,815; 6,783,736; 6,783,736; 6,664,104; 6,921,639; 7,309,409; 7,294,478; 7,208,072; 7,622,083; 7,854,897; 7,491,527; 8,168,442; 7,754,476; 7,435,575; 8,178,056; 7,727,472; 7,678,576; 7,553,647; 7,858,045; 7,988,913; 8,105,783; 8,551,761; 8,354,080; 8,623,789; 8,470,153; 8,415,103; 8,317,728; 8,114,027; 5,627,071; 8,632,740; 8,460,620; 8,425,864; and 8,226,906.

What is claimed is:

1. A reaction cartridge comprising:
a pressurizable first chamber;
a first pressure actuator in fluid communication with the first chamber;
a first valve in fluid communication with the first chamber;
a second valve in fluid communication with the first valve;
a reversibly pressurizable second chamber in fluid communication with the first valve and the second valve;
a second pressure actuator in fluid communication with the second chamber;
a reversibly pressurizable third chamber in fluid communication with the second valve;
a third pressure actuator in fluid communication with the third chamber;
a third valve in fluid communication with the second valve and the third chamber; and
a fourth chamber in fluid communication with the third valve, wherein:
pressurizing the first chamber through the first pressure actuator with the first valve open and with the second valve closed moves liquid from the first chamber to the second chamber;
pressurizing the second chamber through the second pressure actuator with the second valve open and with the first valve and the third valve closed moves liquid from the second chamber to the third chamber;
pressurizing the third chamber through the third pressure actuator with the second valve open and with the first valve and the third valve closed moves liquid from the third chamber to the second chamber; and
pressurizing the third chamber through the third pressure actuator with the second valve closed and the third valve open moves liquid from the third chamber to the fourth chamber.

2. The reaction cartridge of claim 1 wherein a valve selected from the group consisting of the first valve, the second valve, and the third valve is a pneumatically controlled valve.

3. The reaction cartridge of claim 1 wherein the second chamber comprises a dried component selected from the group consisting of a detergent, a reducing agent, and a cell-wall lysis enzyme.

4. The reaction cartridge of claim 1 wherein at least one of the third chamber and the fourth chamber comprises a dried DNA polymerase.

5. The reaction cartridge of claim 1 wherein the fourth chamber comprises a dried component selected from the group consisting of a primer and a DNA detection reagent.

6. The reaction cartridge of claim 1 wherein the fourth chamber comprises multiple fourth chambers.

7. The reaction cartridge of claim 1 wherein the fourth chamber comprises multiple fourth chambers wherein at least one of the fourth chambers comprises a primer not included in another of the fourth chambers.

8. A method of detecting an analyte in a sample with the reaction cartridge of claim 1 comprising:
introducing the sample in the first chamber;
pressurizing the first chamber through the first pressure actuator with the first valve open and with the second valve closed to transfer the sample to the second chamber wherein the sample undergoes a first change in composition or constitution;
pressurizing the second chamber through the second pressure actuator with the second valve open and with the first valve and the third valve closed to transfer the sample to the third chamber wherein the sample undergoes a second change in composition or constitution; and
pressurizing the third chamber through the third pressure actuator with the second valve closed and the third valve open to transfer the sample to the fourth chamber; and
detecting the analyte in the fourth chamber.

9. The method of claim 8 further including pressurizing the third chamber through the third pressure actuator with the second valve open and with the first valve and the third valve closed to transfer the sample from the third chamber to the second chamber prior to transferring the sample to the fourth chamber.

10. The method of claim 8 wherein the analyte is a nucleic acid.

11. The method of claim 8 wherein the analyte is a nucleic acid and the detecting the analyte comprises amplifying the nucleic acid.

12. The method of claim 8 wherein the analyte is a nucleic acid and the detecting the analyte comprises isothermally amplifying the nucleic acid.

13. The method of claim 8 wherein the sample comprises a cell or a virion.

14. The method of claim 8 wherein the sample comprises a cell or a virion and the first change in composition or constitution comprises lysis of the cell or virion.

15. A reaction cartridge comprising:
a pressurizable first chamber;
a first pressure actuator in fluid communication with the first chamber;
a first valve in fluid communication with the first chamber;
a second valve in fluid communication with the first valve;
a reversibly pressurizable second chamber in fluid communication with the first valve and the second valve;
a second pressure actuator in fluid communication with the second chamber;

a reversibly pressurizable third chamber in fluid communication with the second valve;
a third pressure actuator in fluid communication with the third chamber;
a third valve in fluid communication with the second valve and the third chamber; and
a fourth chamber in fluid communication with the third valve, wherein:
the first valve is in fluid connection with the second valve via a channel that does not pass through the second chamber;
the second valve is in fluid connection with the third valve via a channel that does not pass through the third chamber; or
the first valve is in fluid connection with the second valve via a channel that does not pass through the second chamber and the second valve is in fluid connection with the third valve via a channel that does not pass through the third chamber.

16. The reaction cartridge of claim 15 wherein the first valve is in direct fluid connection with the second valve, the second valve is in direct fluid connection with the third valve, or the first valve is in direct fluid connection with the second valve and the second valve is in direct fluid connection with the third valve.

17. A reaction cartridge comprising:
a pressurizable first chamber;
a first pressure actuator in fluid communication with the first chamber;
a first valve in fluid communication with the first chamber;
a second valve in fluid communication with the first valve;
a reversibly pressurizable second chamber in fluid communication with the first valve and the second valve;
a second pressure actuator in fluid communication with the second chamber;
a reversibly pressurizable third chamber in fluid communication with the second valve;
a third pressure actuator in fluid communication with the third chamber;
a third valve in fluid communication with the second valve and the third chamber; and
a fourth chamber in fluid communication with the third valve, wherein:
the first valve is in fluid connection with the second valve via a channel that does not pass through the second chamber;
the second valve is in fluid connection with the third valve via a channel that does not pass through the third chamber; or
the first valve is in fluid connection with the second valve via a channel that does not pass through the second chamber and the second valve is in fluid connection
with the third valve via a channel that does not pass through the third chamber, wherein:
pressurizing the first chamber through the first pressure actuator with the first valve open and with the second valve closed moves liquid from the first chamber to the second chamber;
pressurizing the second chamber through the second pressure actuator with the second valve open and with the first valve and the third valve closed moves liquid from the second chamber to the third chamber;
pressurizing the third chamber through the third pressure actuator with the second valve open and with the first valve and the third valve closed moves liquid from the third chamber to the second chamber; and
pressurizing the third chamber through the third pressure actuator with the second valve closed and the third valve open moves liquid from the third chamber to the fourth chamber.

18. The reaction cartridge of claim 15 wherein a valve selected from the group consisting of the first valve, the second valve, and the third valve is a pneumatically controlled valve.

19. The reaction cartridge of claim 15 wherein the second chamber comprises a dried component selected from the group consisting of a detergent, a reducing agent, and a cell-wall lysis enzyme.

20. The reaction cartridge of claim 15 wherein at least one of the third chamber and the fourth chamber comprises a dried DNA polymerase.

21. The reaction cartridge of claim 15 wherein the fourth chamber comprises a dried component selected from the group consisting of a primer and a DNA detection reagent.

22. The reaction cartridge of claim 15 wherein the fourth chamber comprises multiple fourth chambers.

23. The reaction cartridge of claim 15 wherein the fourth chamber comprises multiple fourth chambers wherein at least one of the fourth chambers comprises a primer not included in another of the fourth chambers.

24. A method of detecting an analyte in a sample with the reaction cartridge of claim 15 comprising:
introducing the sample in the first chamber;
pressurizing the first chamber through the first pressure actuator with the first valve open and with the second valve closed to transfer the sample to the second chamber wherein the sample undergoes a first change in composition or constitution;
pressurizing the second chamber through the second pressure actuator with the second valve open and with the first valve and the third valve closed to transfer the sample to the third chamber wherein the sample undergoes a second change in composition or constitution; and
pressurizing the third chamber through the third pressure actuator with the second valve closed and the third valve open to transfer the sample to the fourth chamber; and
detecting the analyte in the fourth chamber.

25. The method of claim 24 further including pressurizing the third chamber through the third pressure actuator with the second valve open and with the first valve and the third valve closed to transfer the sample from the third chamber to the second chamber prior to transferring the sample to the fourth chamber.

26. The method of claim 24 wherein the analyte is a nucleic acid.

27. The method of claim 24 wherein the analyte is a nucleic acid and the detecting the analyte comprises amplifying the nucleic acid.

28. The method of claim 24 wherein the analyte is a nucleic acid and the detecting the analyte comprises isothermally amplifying the nucleic acid.

29. The method of claim 24 wherein the sample comprises a cell or a virion.

30. The method of claim 24 wherein the sample comprises a cell or a virion and the first change in composition or constitution comprises lysis of the cell or virion.

* * * * *